(12) United States Patent
Alvarez et al.

(10) Patent No.: US 7,833,530 B2
(45) Date of Patent: Nov. 16, 2010

(54) METHODS OF INHIBITING THE PSGL-1-MEDIATED ADHESION AND CHEMOKINE-MEDIATED MIGRATION WITH PSGL-1-SPECIFIC ANTIBODIES

(75) Inventors: Richard Alvarez, Edmond, OK (US); Scott Rollins, Oklahoma City, OK (US)

(73) Assignee: Selexys Pharmaceuticals Corporation, Oklahoma City, OK (US)

( * ) Notice: Subject to any disclaimer, the term of this patent is extended or adjusted under 35 U.S.C. 154(b) by 0 days.

(21) Appl. No.: 12/467,060

(22) Filed: May 15, 2009

(65) Prior Publication Data

US 2009/0285812 A1 Nov. 19, 2009

Related U.S. Application Data

(60) Provisional application No. 61/127,791, filed on May 15, 2008.

(51) Int. Cl.
*A61K 39/395* (2006.01)
*C07K 16/28* (2006.01)

(52) U.S. Cl. ............... 424/154.1; 424/130.1; 424/133.1; 424/141.1; 424/143.1; 424/144.1; 424/152.1; 424/153.1; 424/172.1; 424/173.1; 530/387.1; 530/387.3; 530/388.1; 530/388.2; 530/388.22; 530/388.7; 530/388.73; 530/388.75

(58) Field of Classification Search .................. None
See application file for complete search history.

(56) References Cited

U.S. PATENT DOCUMENTS

| | | | |
|---|---|---|---|
| 5,667,988 A | 9/1997 | Barbas et al. | |
| 7,744,888 B2* | 6/2010 | Lin et al. ................. | 424/154.1 |
| 2002/0031508 A1* | 3/2002 | Wagner et al. ............ | 424/94.63 |
| 2002/0086014 A1 | 7/2002 | Korman et al. | |
| 2003/0018181 A1 | 1/2003 | Larsen et al. | |
| 2004/0001839 A1* | 1/2004 | Levanon et al. .......... | 424/178.1 |
| 2004/0002450 A1* | 1/2004 | Lazarovits et al. ............ | 514/12 |
| 2004/0214272 A1 | 10/2004 | La Rosa et al. | |
| 2005/0069955 A1* | 3/2005 | Plaksin et al. ................. | 435/7.1 |
| 2006/0286112 A1 | 12/2006 | Kellermann et al. | |
| 2007/0020624 A1 | 1/2007 | Rubenfield et al. | |
| 2007/0160601 A1 | 7/2007 | Widom et al. | |

2008/0019984 A1 1/2008 Shusta et al.

OTHER PUBLICATIONS

Hirata et al., "Human P-selectin glycoprotein ligand-1 (PSGL-1) interacts with the skin-associated chemokine CCL27 via sulfated tyrosines at the PSGL-1 amino terminus," *J. Biol. Chem.*, (Issue of Dec. 10, 2004) vol. 279, No. 50, pp. 51775-51782.
Inoue, et al., "Blockade of PSGL-1 attenuates DC14+ monocytic cell recruitment in Intestinal mucosa and ameliorates ileitis in SAMP1/Yit mice," *Journal of Leukocyte Biology*, (Mar. 2005) vol. 77, pp. 287-295.
Li et al., "Visualization of P-selectin Glycoprotein Ligand-1 as a Highly Extended Molecule and Mapping of Protein Epitopes for Monoclonal Antibodies," *The Journal of Biological Chemistry*, vol. 271, No. 11, (Issue of Mar. 15, 1996) pp. 6342-6348.
Marini et al., "TNF-α neutralization ameliorates the severity of murine Crohn's-like ileitis by abrogation of intestinal epithelial cell apoptosis," *PNAS*, vol. 100, No. 14, (Jul. 8, 2003) pp. 8366-8371.
Moore et al., "P-Selectin Glycoprotein Ligand-1 Mediates Rolling of Human Neutorphils on P-Selectin," *J. Cell. Biol.*, vol. 128, No. 4 (Feb. 1995) pp. 661-671.
Rivera-Nieves et al., "Critical role of endothelial P-selectin glycoprotein ligand 1 in chronic murine ileitis", *The Journal of Experimental Medicine*, vol, 203, No, 4, (Apr. 17, 2006) pp, 907-917.
Swers, "Isolation and Engineering of a High Affinity Antibody Against P-selectin Glycoprotein Ligand-1 (PSGL-1)," Ph.D. Thesis, *Department of Engineering at Massachusetts Institute of Technology*, (Feb. 18, 2005) pp. 1-96.
Swers et al., "A high affinity human antibody antagonist of P-selectin mediated rolling," *Biochemical and Biophysical Research Communications*, vol. 350, (Aug. 12, 2006) pp. 508-513.
Thatte et al., "Binding of function-blocking mAbs to mouse and human P-selectin glycoprotein ligand-1 peptides with and without tyrosine sulfation," *Journal of Leukocyte Biology*, vol. 72, (Sep. 2002) pp. 470-477.
Veerman et al., "Interaction of the selectin ligand PSGL-1 with chemokines CCL21 and CCL19 facilitates efficient homing of T cells to secondary lymphoid organs," *Nature Immunology*, vol, 8, No. 5 (May 2007) pp. 532-539.
PCT Search Report, PCT/US2009/044188, Dec. 4, 2009.

* cited by examiner

*Primary Examiner*—Phillip Gambel
(74) *Attorney, Agent, or Firm*—Dunlap Codding, P.C.

(57) ABSTRACT

The present invention is directed to antibodies and binding fragments thereof, which bind with high affinity and specificity to human P-selectin glycoprotein ligand 1 (PSGL-1) and which block both selectin and chemokine binding to PSGL-1 expressed on leukocytes, lymphocytes and endothelial cells and thus which inhibit migration and/or rolling of these cells and to methods for screening for such antibodies and binding fragments thereof and to methods of therapeutic use thereof.

29 Claims, 9 Drawing Sheets

42                          49                                              62
QATEYEYLDYDFLPETEPPEM
         PL1 epitope 42                          49                                              62
QATEYEYLDYDFLPETEPPEM
         KPL1 epitope 42                          49                                              62
QATEYEYLDYDFLPETEPPEM
                    SelK1 epitope 42                          49                                              62
QATEYEYLDYDFLPETEPPEM
         Chemokine epitope Antibody and Chemokine Binding Epitopes of Human
PSGL-1 (Amino Acids 42-62 of SEQ ID NO:1)

Figure 1

SelK1 Heavy Chain

```
                           Signal Peptide
        M   K   C   S   W   V   I   F   F   L   M   A   V   V   T   G   V   N   S   Q
  1     atgaaatgcagctgggtaattttttttctcatggccgtagttacaggcgtcaattcacaa         60
                              VH
        V   Q   L   Q   Q   S   G   P   G   L   V   K   P   S   Q   T   L   S   L   T
 61     gttcaacttcaacaatcaggcccaggactcgtaaaaccatcacaaacactctcactcaca         120

C   A   I   S   G   D   S   V   S   S   N   I   A   A   W   H   W   I   R   L
121     tgcgctatttcaggcgattccgttagctccaacatagcagcttggcattggatcagactt         180

S   P   S   R   G   L   E   W   L   G   R   T   Y   Y   R   R   S   K   W   N
181     tcaccatcaagaggactcgaatggctcggacgaacatactatagaagatcaaaatggaac         240

Y   D   Y   A   L   S   V   K   S   R   I   N   I   N   P   D   T   S   K   N
241     tatgactacgccctctctgttaaatcacgcatcaatattaatcccgacacatctaaaaat         300

L   F   S   L   Q   L   N   S   V   T   P   E   D   T   A   V   Y   Y   C   T
301     ctcttttcactgcaacttaattcagtcaccccgaagatacagccgtctattattgcaca         360

R   G   G   G   R   A   H   S   A   W   G   Q   G   T   L   V   T   V   S   S
361     cgcggcggaggaagagcccactcagcatggggacaaggtacactcgttaccgtttctagc         420
                                                            CH1
        A   S   T   K   G   P   S   V   F   P   L   A   P   C   S   R   S   T   S   E
421     gcttccacaaaaggtccttccgtcttcccacttgctccctgttctcgctcaacttcagaa         480

S   T   A   A   L   G   C   L   V   K   D   Y   F   P   E   P   V   T   V   S
481     tccaccgccgcccttggatgtctcgtcaaagattatttccctgaacccgttaccgtatcc         540

W   N   S   G   A   L   T   S   G   V   H   T   F   P   A   V   L   Q   S   S
541     tggaactccggcgccctcacctcaggagtccacaccttccctgccgttcttcaaagttct         600

G   L   Y   S   L   S   S   V   V   T   V   T   S   S   N   F   G   T   Q   T
601     ggcctgtactccctctcctcagttgttaccgttacaagctctaatttcggaacccaaact         660

Y   T   C   N   V   D   H   K   P   S   N   T   K   V   D   K   T   V   E   R
661     tatacctgcaatgtagaccataaacctagcaatacaaaagtcgataaaacagtagaacgt         720
                      Hinge
        K   C   C   V   E   C   P   P   C   P   A   P   P   V   A   G   P   S   V   F
721     aaatgttgtgtagaatgccctccatgccccgcccccccagtcgccggcccttcagttttc         780
```

Figure 8A

```
                        CH2
       L  F  P  P  K  P  K  D  T  L  M  I  S  R  T  P  E  V  T  C
 781   cttttccccctaagcccaaagacacccttatgatctcccgaacacctgaggtcacgtgc   840

V  V  V  D  V  S  H  E  D  P  E  V  Q  F  N  W  Y  V  D  G
 841   gtggtggtggacgtgagccacgaagaccccgaggtccagttcaactggtacgtggacggc   900

M  E  V  H  N  A  K  T  K  P  R  E  E  Q  F  N  S  T  F  R
 901   atggaggtgcataatgccaagacaaagccacgggaggagcagttcaacagcacgttccgt   960

V  V  S  V  L  T  V  V  H  Q  D  W  L  N  G  K  E  Y  K  C
 961   gtggtcagcgtcctcaccgtcgtgcaccaggactggctgaacggcaaggagtacaagtgc   1020

A  V  S  N  K  G  L  P  A  P  I  E  K  T  I  S  K  T  K  G
1021   gcggtctccaacaaaggcctcccagcccccatcgagaaaaccatctccaaaaccaaaggg   1080

CH3
       Q  P  R  E  P  Q  V  Y  T  L  P  P  S  R  E  E  M  T  K  N
1081   cagccccgagaaccacaggtgtacaccctgccccccatcccgggaggagatgaccaagaac   1140

Q  V  S  L  T  C  L  V  K  G  F  Y  P  S  D  I  A  V  E  W
1141   caggtcagcctgacctgcctggtcaaaggcttctaccccagcgacatcgccgtggagtgg   1200

E  S  N  G  Q  P  E  N  N  Y  K  T  T  P  P  M  L  D  S  D
1201   gagagcaatgggcagccggagaacaactacaagaccacacctcccatgctggactccgac   1260

G  S  F  F  L  Y  S  K  L  T  V  D  K  S  R  W  Q  Q  G  N
1261   ggctccttcttcctctacagcaagctcaccgtggacaagagcaggtggcagcaggggaac   1320

V  F  S  C  S  V  M  H  E  A  L  H  N  H  Y  T  Q  K  S  L
1321   gtcttctcatgctccgtgatgcatgaggctctgcacaaccactacacacagaagagcctc   1380

S  L  S  P  G  K  *
1381   tccctgtctccgggtaaatga   1401
```

Figure 8B

SelK1 Light Chain

```
                            Signal Peptide
      M   E   S   Q   T   Q   V   F   V   Y   M   L   L   W   L   S   G   V   D   G
  1   atggaatctcagactcaagttttcgtttacatgttgttgtggctctccggcgtggatggc   60
                                 VL
      E   I   V   L   T   Q   S   P   G   T   L   S   V   S   P   G   E   R   A   T
 61   gaaattgtactcacccaaagccccggaacactctcagtatcccccggtgaaagagctacc   120

L   S   C   R   A   S   Q   S   V   S   R   S   H   L   A   W   Y   Q   Q   K
121   ctctcatgtagagcatctcaatccgtctctcgatcacatctcgcatggtatcaacaaaaa   180

P   G   Q   A   P   R   L   L   I   F   G   A   S   S   R   A   T   G   I   P
181   cctggacaagcaccacgacttcttatattcggcgcctcatcaagagctaccggcatccca   240

D   R   F   S   G   S   G   S   G   T   D   F   T   L   T   I   S   R   L   E
241   gacagattttcaggcagcggctccggcacagattttaccctcactatatcccgactcgaa   300

P   E   D   F   A   V   Y   Y   C   Q   Q   Y   G   R   P   G   V   T   F   G
301   ccagaagactttgcagtatactactgtcagcaatacggacgacctggcgttacattcgga   360

Q   G   T   K   V   E   I   K   R   T   V   A   A   P   S   V   F   I   F   P
361   caaggaacaaaagttgaaattaagcgcaccgtagccgcaccttcagtatttatctttccc   420
                                     CL
      P   S   D   E   Q   L   K   S   G   T   A   S   V   V   C   L   L   N   N   F
421   ccatcagacgaacaactcaaatcaggaaccgcatcagtagtttgccttctcaataatttt   480

Y   P   R   E   A   K   V   Q   W   K   V   D   N   A   L   Q   S   G   N   S
481   tatccccgtgaagccaaagttcaatggaaagtcgacaatgcccttcagtcaggaaatagt   540

Q   E   S   V   T   E   Q   D   S   K   D   S   T   Y   S   L   S   S   T   L
541   caagaatcagtcacagaacaagatagcaaagactcaacatactcactttcatcaactctt   600

T   L   S   K   A   D   Y   E   K   H   K   V   Y   A   C   E   V   T   H   Q
601   actctctcaaaagccgattacgaaaaacacaaagtttatgcatgcgaagttacacaccaa   660

G   L   S   S   P   V   T   K   S   F   N   R   G   E   C   *
661   ggactttcatctccagttacaaaatcatttaaccgcggcgaatgctag   708
```

Figure 9

```
                        SEQUENCE LISTING

<160> NUMBER OF SEQ ID NOS: 13

<210> SEQ ID NO 1
<211> LENGTH: 412
<212> TYPE: PRT
<213> ORGANISM: Homo sapiens

<400> SEQUENCE: 1

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
                35                  40                  45

Leu Asp Tyr Asp Phe Leu Pro Glu Thr Glu Pro Pro Glu Met Leu Arg
        50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
                100                 105                 110

Ser Thr Asp Ser Ala Ala Met Glu Ile Gln Thr Thr Gln Pro Ala Ala
            115                 120                 125

Thr Glu Ala Gln Thr Thr Gln Pro Val Pro Thr Glu Ala Gln Thr Thr
    130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
                165                 170                 175

Ala Ala Thr Glu Ala Gln Thr Thr Gln Pro Thr Gly Leu Glu Ala Gln
                180                 185                 190

Thr Thr Ala Pro Ala Ala Met Glu Ala Gln Thr Thr Ala Pro Ala Ala
            195                 200                 205

Met Glu Ala Gln Thr Thr Pro Pro Ala Ala Met Glu Ala Gln Thr Thr
    210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
                245                 250                 255
```

```
Ala Ala Met Glu Ala Leu Ser Thr Glu Pro Ser Ala Thr Glu Ala Leu
            260                 265                 270

Ser Met Glu Pro Thr Thr Lys Arg Gly Leu Phe Ile Pro Phe Ser Val
            275                 280                 285

Ser Ser Val Thr His Lys Gly Ile Pro Met Ala Ala Ser Asn Leu Ser
        290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
                325                 330                 335

Cys Thr Val Val Leu Ala Val Arg Leu Ser Arg Lys Gly His Met Tyr
                340                 345                 350

Pro Val Arg Asn Tyr Ser Pro Thr Glu Met Val Cys Ile Ser Ser Leu
            355                 360                 365

Leu Pro Asp Gly Gly Glu Gly Pro Ser Ala Thr Ala Asn Gly Gly Leu
        370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
                405                 410

<210> SEQ ID NO 2
<211> LENGTH: 466
<212> TYPE: PRT
<213> ORGANISM: Homo sapiens

<400> SEQUENCE: 2

Met Lys Cys Ser Trp Val Ile Phe Phe Leu Met Ala Val Val Thr Gly
1               5                   10                  15

Val Asn Ser Gln Val Gln Leu Gln Gln Ser Gly Pro Gly Leu Val Lys
            20                  25                  30

Pro Ser Gln Thr Leu Ser Leu Thr Cys Ala Ile Ser Gly Asp Ser Val
        35                  40                  45

Ser Ser Asn Ile Ala Ala Trp His Trp Ile Arg Leu Ser Pro Ser Arg
    50                  55                  60

Gly Leu Glu Trp Leu Gly Arg Thr Tyr Tyr Arg Ser Lys Trp Asn
65                  70                  75                  80

Tyr Asp Tyr Ala Leu Ser Val Lys Ser Arg Ile Asn Ile Asn Pro Asp
                85                  90                  95

Thr Ser Lys Asn Leu Phe Ser Leu Gln Leu Asn Ser Val Thr Pro Glu
            100                 105                 110

Asp Thr Ala Val Tyr Tyr Cys Thr Arg Gly Gly Gly Arg Ala His Ser
        115                 120                 125

Ala Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Thr Ser Ser Asn Phe Gly Thr Gln Thr Tyr Thr Cys Asn
    210                 215                 220
```

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
            245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Met Glu Val His
        290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Ala Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 3
<211> LENGTH: 1401
<212> TYPE: DNA
<213> ORGANISM: Homo sapiens

<400> SEQUENCE: 3
atgaaatgca gctgggtaat ttttttttctc atggccgtag ttacaggcgt caattcacaa      60
gttcaacttc aacaatcagg cccaggactc gtaaaaccat cacaaacact ctcactcaca     120
tgcgctattt caggcgattc cgttagctcc aacatagcag cttggcattg gatcagactt     180
tcaccatcaa gaggactcga atggctcgga cgaacatact atagaagatc aaaatggaac     240
tatgactacg ccctctctgt taaatcacgc atcaatatta atcccgacac atctaaaaat     300
ctcttttcac tgcaacttaa ttcagtcacc cccgaagata cagccgtcta ttattgcaca     360
cgcggcggag gaagagccca ctcagcatgg ggacaaggta cactcgttac cgtttctagc     420
gcttccacaa aggtccttc cgtcttccca cttgctccct gttctcgctc aacttcagaa     480
tccaccgccg cccttggatg tctcgtcaaa gattatttcc ctgaaccgt taccgtatcc     540 tggaactccg gcgccctcac ctcaggagtc cacaccttcc ctgccgttct tcaaagttct     600
ggcctgtact ccctctcctc agttgttacc gttacaagct ctaatttcgg aacccaaact     660

```
tatacctgca atgtagacca taaacctagc aatacaaaag tcgataaaac agtagaacgt    720
aaatgttgtg tagaatgccc tccatgcccc gccccccag tcgccggccc ttcagttttc     780 cttttcccc ctaagcccaa agacacccctt atgatctccc gaacacctga ggtcacgtgc    840
gtggtggtgg acgtgagcca cgaagacccc gaggtccagt tcaactggta cgtggacggc    900
atggaggtgc ataatgccaa gacaaagcca cgggaggagc agttcaacag cacgttccgt    960
gtggtcagcg tcctcaccgt cgtgcaccag gactggctga acggcaagga gtacaagtgc   1020
gcggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac tcccatgct ggactccgac    1260 ggctccttct tcctctacag caagctcacc gtggacaaga gcaggtggca gcaggggaac   1320
gtcttctcat gctccgtgat gcatgaggct ctgcacaacc actacacaca gaagagcctc   1380
tccctgtctc cgggtaaatg a                                              1401

<210> SEQ ID NO 4
<211> LENGTH: 235
<212> TYPE: PRT
<213> ORGANISM: Homo sapiens

<400> SEQUENCE: 4

Met Glu Ser Gln Thr Gln Val Phe Val Tyr Met Leu Leu Trp Leu Ser
1               5                   10                  15

Gly Val Asp Gly Glu Ile Val Leu Thr Gln Ser Pro Gly Thr Leu Ser
                20                  25                  30

Val Ser Pro Gly Glu Arg Ala Thr Leu Ser Cys Arg Ala Ser Gln Ser
            35                  40                  45

Val Ser Arg Ser His Leu Ala Trp Tyr Gln Gln Lys Pro Gly Gln Ala
        50                  55                  60

Pro Arg Leu Leu Ile Phe Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Arg Pro Gly Val Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

```
<210> SEQ ID NO 5
<211> LENGTH: 708
<212> TYPE: DNA
<213> ORGANISM: Homo sapiens

<400> SEQUENCE: 5
atggaatctc agactcaagt tttcgtttac atgttgttgt ggctctccgg cgtggatggc      60
gaaattgtac tcacccaaag ccccggaaca ctctcagtat cccccggtga aagagctacc     120
ctctcatgta gagcatctca atccgtctct cgatcacatc tcgcatggta tcaacaaaaa     180
cctggacaag caccacgact tcttatattc ggcgcctcat caagagctac cggcatccca     240
gacagatttt caggcagcgg ctccggcaca gattttaccc tcactatatc ccgactcgaa     300
ccagaagact ttgcagtata ctactgtcag caatacggac gacctggcgt acatattcgga    360 caaggaacaa agttgaaat taagcgcacc gtagccgcac cttcagtatt tatctttccc     420
ccatcagacg aacaactcaa atcaggaacc gcatcagtag tttgccttct caataatttt     480
tatccccgtg aagccaaagt tcaatggaaa gtcgacaatg cccttcagtc aggaaatagt     540
caagaatcag tcacagaaca agatagcaaa gactcaacat actcactttc atcaactctt     600
actctctcaa aagccgatta cgaaaaacac aaagtttatg catgcgaagt tacacaccaa     660
ggactttcat ctccagttac aaaatcattt aaccgcggcg aatgctag                 708

<210> SEQ ID NO 6
<211> LENGTH: 7
<212> TYPE: PRT
<213> ORGANISM: Homo sapiens

<400> SEQUENCE: 6

Ser Asn Ile Ala Ala Trp His
1               5

<210> SEQ ID NO 7
<211> LENGTH: 19
<212> TYPE: PRT
<213> ORGANISM: Homo sapiens

<400> SEQUENCE: 7

Arg Thr Tyr Tyr Arg Arg Ser Lys Trp Asn Tyr Asp Tyr Ala Leu Ser
1               5                   10                  15

Val Lys Ser

<210> SEQ ID NO 8
<211> LENGTH: 8
<212> TYPE: PRT
<213> ORGANISM: Homo sapiens

<400> SEQUENCE: 8

Gly Gly Gly Arg Ala His Ser Ala
1               5

<210> SEQ ID NO 9
<211> LENGTH: 12
<212> TYPE: PRT
<213> ORGANISM: Homo sapiens

<400> SEQUENCE: 9

Arg Ala Ser Gln Ser Val Ser Arg Ser His Leu Ala
1               5                   10
```

```
<210> SEQ ID NO 10
<211> LENGTH: 7
<212> TYPE: PRT
<213> ORGANISM: Homo sapiens

<400> SEQUENCE: 10

Gly Ala Ser Ser Arg Ala Thr
1               5

<210> SEQ ID NO 11
<211> LENGTH: 9
<212> TYPE: PRT
<213> ORGANISM: Homo sapiens

<400> SEQUENCE: 11

Gln Gln Tyr Gly Arg Pro Gly Val Thr
1               5

<210> SEQ ID NO 12
<211> LENGTH: 4828
<212> TYPE: DNA
<213> ORGANISM: Homo sapiens

<400> SEQUENCE: 12
ggatctgcga tcgctccggt gcccgtcagt gggcagagcg cacatcgccc acagtccccg    60
agaagttggg gggaggggtc ggcaattgaa cgggtgccta gagaaggtgg cgcggggtaa   120
actgggaaag tgatgtcgtg tactggctcc gccttttttcc cgagggtggg ggagaaccgt   180
atataagtgc agtagtcgcc gtgaacgttc tttttcgcaa cgggtttgcc gccagaacac   240
agctgaagct tcgaggggct cgcatctctc cttcacgcgc ccgccgccct acctgaggcc   300
gccatccacg ccggttgagt cgcgttctgc cgcctcccgc ctgtggtgcc tcctgaactg   360
cgtccgccgt ctaggtaagt ttaaagctca ggtcgagacc gggcctttgt ccggcgctcc   420
cttggagcct acctagactc agccggctct ccacgctttg cctgaccctg cttgctcaac   480
tctacgtctt tgtttcgttt tctgttctgc gccgttacag atccaagctg tgaccggcgc   540
ctacctgaga tcaccggtgc caccatgaaa tgcagctggg taatttttttt tctcatggcc   600 gtagttacag gcgtcaattc acaagttcaa cttcaacaat caggcccagg actcgtaaaa   660
ccatcacaaa cactctcact cacatgcgct atttcaggcg attccgttag ctccaacata   720
gcagcttggc attggatcag acttttcacca tcaagaggac tcgaatggct cggacgaaca   780
tactatagaa gatcaaaatg gaactatgac tacgccctct ctgttaaatc acgcatcaat   840
attaatcccg acacatctaa aaatctcttt tcactgcaac ttaattcagt caccccgaa    900 gatacagccg tctattattg cacacgcggc ggaggaagag cccactcagc atggggacaa   960
ggtacactcg ttaccgtttc tagcgcttcc acaaaaggtc cttccgtctt cccacttgct  1020
ccctgttctc gctcaacttc agaatccacc gccgcccttg gatgtctcgt caaagattat  1080
ttccctgaac ccgttaccgt atcctggaac tccggcgccc tcacctcagg agtccacacc  1140
ttccctgccg ttcttcaaag ttctggcctg tactccctct cctcagttgt taccgttaca  1200
agctctaatt tcggaaccca aacttatacc tgcaatgtag accataaacc tagcaataca  1260
aaagtcgata aaacagtaga acgtaaatgt tgtgtagaat gccctccatg ccccgccccc  1320
ccagtcgccg gcccttcagt tttccttttt ccccctaagc ccaaagacac ccttatgatc  1380
tcccgaacac ctgaggtcac gtgcgtggtg gtggacgtga gccacgaaga ccccgaggtc  1440
cagttcaact ggtacgtgga cggcatggag gtgcataatg ccaagacaaa gccacgggag  1500
```

```
gagcagttca acagcacgtt ccgtgtggtc agcgtcctca ccgtcgtgca ccaggactgg    1560
ctgaacggca aggagtacaa gtgcgcggtc tccaacaaag gcctcccagc ccccatcgag    1620
aaaaccatct ccaaaaccaa agggcagccc cgagaaccac aggtgtacac cctgccccca    1680
tcccgggagg agatgaccaa gaaccaggtc agcctgacct gcctggtcaa aggcttctac    1740
cccagcgaca tcgccgtgga gtgggagagc aatgggcagc cggagaacaa ctacaagacc    1800
acacctccca tgctggactc cgacggctcc ttcttcctct acagcaagct caccgtggac    1860
aagagcaggt ggcagcaggg gaacgtcttc tcatgctccg tgatgcatga ggctctgcac    1920
aaccactaca cacagaagag cctctccctg tctccgggta atgagtgcc acggctagct    1980 ggccagacat gataagatac attgatgagt ttggacaaac cacaactaga atgcagtgaa    2040
aaaaatgctt tatttgtgaa atttgtgatg ctattgcttt atttgtaacc attataagct    2100
gcaataaaca agttaacaac aacaattgca ttcattttat gtttcaggtt caggggagg    2160 tgtgggaggt ttttaaagc aagtaaaacc tctacaaatg tggtatggaa ttaattctaa    2220
aatacagcat agcaaaactt taacctccaa atcaagcctc tacttgaatc cttttctgag    2280
ggatgaataa ggcataggca tcaggggctg ttgccaatgt gcattagctg tttgcagcct    2340
caccttcttt catggagttt aagatatagt gtattttccc aaggtttgaa ctagctcttc    2400
atttctttat gttttaaatg cactgacctc ccacattccc tttttagtaa aatattcaga    2460
aataatttaa atacatcatt gcaatgaaaa taaatgtttt ttattaggca gaatccagat    2520
gctcaaggcc cttcataata tcccccagtt tagtagttgg acttagggaa caaaggaacc    2580
tttaatagaa attggacagc aagaaagcga gcttctagct tatcctcagt cctgctcctc    2640
tgccacaaag tgcacgcagt tgccggccgg gtcgcgcagg gcgaactccc gcccccacgg    2700
ctgctcgccg atctcggtca tggccggccc ggaggcgtcc cggaagttcg tggacacgac    2760
ctccgaccac tcggcgtaca gctcgtccag gccgcgcacc cacacccagg ccagggtgtt    2820
gtccggcacc acctggtcct ggaccgcgct gatgaacagg gtcacgtcgt cccggaccac    2880
accggcgaag tcgtcctcca cgaagtcccg ggagaacccg agccggtcgg tccagaactc    2940
gaccgctccg gcgacgtcgc gcgcggtgag caccggaacg gcactggtca acttggccat    3000
gatggctcct cctgtcagga gaggaaagag aagaaggtta gtacaattgc tatagtgagt    3060
tgtattatac tatgcagata tactatgcca atgattaatt gtcaaactag ggctgcaggg    3120
ttcatagtgc cactttttcct gcactgcccc atctcctgcc cacccttttcc caggcataga    3180 cagtcagtga cttaccaaac tcacaggagg gagaaggcag aagcttgaga cagacccgcg    3240
ggaccgccga actgcgaggg gacgtggcta gggcggcttc ttttatggtg cgccggccct    3300
cggaggcagg gcgctcgggg aggcctagcg gccaatctgc ggtggcagga ggcggggccg    3360
aaggccgtgc ctgaccaatc cggagcacat aggagtctca gcccccgcc ccaaagcaag    3420 gggaagtcac gcgcctgtag cgccagcgtg ttgtgaaatg ggggcttggg ggggttgggg    3480
ccctgactag tcaaaacaaa ctcccattga cgtcaatggg gtggagactt ggaaatcccc    3540
gtgagtcaaa ccgctatcca cgcccattga tgtactgcca aaaccgcatc atcatggtaa    3600
tagcgatgac taatacgtag atgtactgcc aagtaggaaa gtcccataag gtcatgtact    3660
gggcataatg ccaggcgggc catttaccgt cattgacgtc aataggggc gtacttggca    3720 tatgatacac ttgatgtact gccaagtggg cagtttaccg taaatactcc acccattgac    3780
gtcaatggaa agtccctatt ggcgttacta tgggaacata cgtcattatt gacgtcaatg    3840
ggcgggggtc gttgggcggt cagccaggcg ggccatttac cgtaagttat gtaacgcctg    3900
```

-continued

| | |
|---|---|
| caggttaatt aagaacatgt gagcaaaagg ccagcaaaag gccaggaacc gtaaaaaggc | 3960 |
| cgcgttgctg gcgttttttcc ataggctccg ccccctgac gagcatcaca aaaatcgacg | 4020 |
| ctcaagtcag aggtggcgaa acccgacagg actataaaga taccaggcgt ttccccctgg | 4080 |
| aagctccctc gtgcgctctc ctgttccgac cctgccgctt accggatacc tgtccgcctt | 4140 |
| tctcccttcg ggaagcgtgg cgctttctca tagctcacgc tgtaggtatc tcagttcggt | 4200 |
| gtaggtcgtt cgctccaagc tgggctgtgt gcacgaaccc ccgttcagc ccgaccgctg | 4260 |
| cgccttatcc ggtaactatc gtcttgagtc caacccggta agacgact tatcgccact | 4320 |
| ggcagcagcc actggtaaca ggattagcag agcgaggtat gtaggcggtg ctacagagtt | 4380 |
| cttgaagtgg tggcctaact acggctacac tagaagaaca gtatttggta tctgcgctct | 4440 |
| gctgaagcca gttaccttcg gaaaaagagt tggtagctct tgatccggca aacaaaccac | 4500 |
| cgctggtagc ggtggttttt tgtttgcaa gcagcagatt acgcgcagaa aaaaggatc | 4560 |
| tcaagaagat cctttgatct tttctacggg gtctgacgct cagtggaacg aaaactcacg | 4620 |
| ttaagggatt ttggtcatgg ctagttaatt aacatttaaa tcagcggccg caataaaata | 4680 |
| tctttatttt cattacatct gtgtgttggt tttttgtgtg aatcgtaact aacatacgct | 4740 |
| ctccatcaaa acaaaacgaa acaaaacaaa ctagcaaaat aggctgtccc cagtgcaagt | 4800 |
| gcaggtgcca gaacatttct ctatcgaa | 4828 |

<210> SEQ ID NO 13
<211> LENGTH: 4127
<212> TYPE: DNA
<213> ORGANISM: Homo sapiens

<400> SEQUENCE: 13

| | |
|---|---|
| ggatctgcga tcgctccggt gcccgtcagt gggcagagcg cacatcgccc acagtccccg | 60 |
| agaagttggg gggagggggtc ggcaattgaa cgggtgccta gagaaggtgg cgcggggtaa | 120 |
| actgggaaag tgatgtcgtg tactggctcc gccttttttcc cgagggtggg ggagaaccgt | 180 |
| atataagtgc agtagtcgcc gtgaacgttc ttttttcgcaa cgggtttgcc gccagaacac | 240 |
| agctgaagct tcgaggggct cgcatctctc cttcacgcgc ccgccgccct acctgaggcc | 300 |
| gccatccacg ccgttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt ctgttctgc gccgttacag atccaagctg tgaccggcgc | 540 |
| ctacctgaga tcaccggtgc caccatggaa tctcagactc aagttttcgt ttacatgttg | 600 |
| ttgtggctct ccggcgtgga tggcgaaatt gtactcaccc aaagcccgg aacactctca | 660 |
| gtatcccccg tgaaagagc taccctctca tgtagagcat ctcaatccgt ctctcgatca | 720 |
| catctcgcat ggtatcaaca aaaacctgga caagcaccac gacttcttat attcggcgcc | 780 |
| tcatcaagag ctaccggcat cccagacaga ttttcaggca gcggctccgg cacagatttt | 840 |
| accctcacta tatcccgact cgaaccagaa gactttgcag tatactactg tcagcaatac | 900 |
| ggacgacctg gcgttacatt cggacaagga acaaaagttg aaattaagcg caccgtagcc | 960 |
| gcaccttcag tatttatctt tccccccatca gacgaacaac tcaaatcagg aaccgcatca | 1020 |
| gtagtttgcc ttctcaataa ttttttatccc cgtgaagcca agttcaatg gaaagtcgac | 1080 |
| aatgcccttc agtcaggaaa tagtcaagaa tcagtcacag aacaagatag caaagactca | 1140 |

```
acatactcac tttcatcaac tcttactctc tcaaaagccg attacgaaaa acacaaagtt    1200
tatgcatgcg aagttacaca ccaaggactt tcatctccag ttacaaaatc atttaaccgc    1260
ggcgaatgct aggctagctg gccagacatg ataagataca ttgatgagtt tggacaaacc    1320
acaactagaa tgcagtgaaa aaatgctttt atttgtgaaa tttgtgatgc tattgcttta    1380
tttgtaacca ttataagctg caataaacaa gttaacaaca acaattgcat tcattttatg    1440
tttcaggttc aggggagggt gtgggaggtt ttttaaagca agtaaaacct ctacaaatgt    1500
ggtatggaat taattctaaa atacagcata gcaaaacttt aacctccaaa tcaagcctct    1560
acttgaatcc ttttctgagg gatgaataag gcataggcat caggggctgt tgccaatgtg    1620
cattagctgt ttgcagcctc accttctttc atggagttta agatatagtg tattttccca    1680
aggtttgaac tagctcttca tttcttatg ttttaaatgc actgacctcc cacattccct    1740
ttttagtaaa atattcagaa ataatttaaa tacatcattg caatgaaaat aaatgttttt    1800
tattaggcag aatccagatg ctcaaggccc ttcataatat cccccagttt agtagttgga    1860
cttagggaac aaaggaacct ttaatagaaa ttggacagca agaaagcgag cttctagctt    1920
atcctcagtc ctgctcctct gccacaaagt gcacgcagtt gccggccggg tcgcgcaggg    1980
cgaactcccg cccccacggc tgctcgccga tctcggtcat ggccggcccg gaggcgtccc    2040
ggaagttcgt ggacacgacc tccgaccact cggcgtacag ctcgtccagg ccgcgcaccc    2100
acacccaggc cagggtgttg tccggcacca cctggtcctg gaccgcgctg atgaacaggg    2160
tcacgtcgtc ccggaccaca ccggcgaagt cgtcctccac gaagtcccgg agaacccga    2220 gccggtcggt ccagaactcg accgctccgg cgacgtcgcg cgcggtgagc accggaacgg    2280
cactggtcaa cttggccatg atggctcctc ctgtcaggag aggaaagaga agaaggttag    2340
tacaattgct atagtgagtt gtattatact atgcagatat actatgccaa tgattaattg    2400
tcaaactagg gctgcagggt tcatagtgcc acttttcctg cactgcccca tctcctgccc    2460
acccttttcc aggcatagac agtcagtgac ttaccaaact cacaggaggg agaaggcaga    2520
agcttgagac agaccccgcgg gaccgccgaa ctgcgagggg acgtggctag gcggcttct    2580 tttatggtgc gccggccctc ggaggcaggg cgctcgggga ggcctagcgg ccaatctgcg    2640
gtggcaggag gcggggccga aggccgtgcc tgaccaatcc ggagcacata ggagtctcag    2700
ccccccgccc caaagcaagg ggaagtcacg cgcctgtagc gccagcgtgt tgtgaaatgg    2760
gggcttgggg gggttggggc cctgactagt caaaacaaac tcccattgac gtcaatgggg    2820
tggagacttg gaaatccccg tgagtcaaac cgctatccac gcccattgat gtactgccaa    2880
aaccgcatca tcatggtaat agcgatgact aatacgtaga tgtactgcca agtaggaaag    2940
tcccataagg tcatgtactg gcataatgc caggcgggcc atttaccgtc attgacgtca    3000 ataggggggcg tacttggcat atgatacact tgatgtactg ccaagtgggc agtttaccgt    3060
aaatactcca cccattgacg tcaatggaaa gtccctattg gcgttactat gggaacatac    3120
gtcattattg acgtcaatgg gcgggggtcg ttgggcggtc agccaggcgg gccatttacc    3180
gtaagttatg taacgcctgc aggttaatta agaaacatgt gagcaaaaggc cagcaaaagg    3240 ccaggaaccg taaaaaggcc gcgttgctgg cgttttttcca taggctccgc cccctgacg    3300 agcatcacaa aaatcgacgc tcaagtcaga ggtggcgaaa cccgacagga ctataaagat    3360
accaggcgtt tccccctgga agctccctcg tgcgctctcc tgttccgacc ctgccgctta    3420
ccggatacct gtccgccttt ctcccttcgg aagcgtggc gctttctcat agctcacgct    3480
gtaggtatct cagttcggtg taggtcgttc gctccaagct gggctgtgtg cacgaacccc    3540
```

```
                                        -continued ccgttcagcc cgaccgctgc gccttatccg gtaactatcg tcttgagtcc aacccggtaa      3600
gacacgactt atcgccactg gcagcagcca ctggtaacag gattagcaga gcgaggtatg      3660
taggcggtgc tacagagttc ttgaagtggt ggcctaacta cggctacact agaagaacag      3720
tatttggtat ctgcgctctg ctgaagccag ttaccttcgg aaaaagagtt ggtagctctt      3780
gatccggcaa acaaaccacc gctggtagcg gtggtttttt tgtttgcaag cagcagatta      3840
cgcgcagaaa aaaaggatct caagaagatc ctttgatctt ttctacgggg tctgacgctc      3900
agtggaacga aaactcacgt taagggattt tggtcatggc tagttaatta acatttaaat      3960
cagcggccgc aataaaatat ctttattttc attacatctg tgtgttggtt ttttgtgtga      4020
atcgtaacta acatacgctc tccatcaaaa caaaacgaaa caaaacaaac tagcaaaata      4080
ggctgtcccc agtgcaagtg caggtgccag aacatttctc tatcgaa                   4127
```

METHODS OF INHIBITING THE PSGL-1-MEDIATED ADHESION AND CHEMOKINE-MEDIATED MIGRATION WITH PSGL-1-SPECIFIC ANTIBODIES

CROSS-REFERENCE TO RELATED APPLICATIONS

The present application claims the benefit under 35 U.S.C. 119(e) of U.S. Provisional Application Ser. No. 61/127,791, filed May 15, 2008, the entirety of which is hereby expressly incorporated herein by reference.

BACKGROUND

This invention relates to antibodies and antigen binding fragments thereof which bind to PSGL-1, methods of their use in treating inflammatory and thrombotic conditions, and methods of screening for PSGL-1 inhibitory substances.

Selectins and P-Selectin Glycoprotein Ligand-1 (PSGL-1).

The body regulates inflammatory responses through a series of multistep adhesive and signaling events in response to infection and injury [1-3]. To start this process circulating leukocytes must first adhere to the vascular wall under the shear forces of flow. The selectins mediate this first adhesive step which is characterized by tethering and rolling of leukocytes on endothelial cells, platelets, or other leukocytes [4, 5]. P-selectin is expressed on activated platelets and endothelial cells and binds to ligands on most leukocytes. L-selectin is expressed on most leukocytes and binds to ligands on some endothelial cells and on other leukocytes. E-selectin is expressed on cytokine-activated endothelial cells and also binds to ligands on most leukocytes. The expression of the selectins and their ligands is tightly regulated to initiate and terminate the inflammatory response. Inappropriate expression of these molecules contributes to leukocyte-mediated tissue damage in many inflammatory and thrombotic disorders [6].

All three selectins are type 1 membrane glycoproteins with an $NH_2$-terminal C-type lectin domain, an EGF-like domain, a varying series of short consensus repeats, a transmembrane domain, and a short cytoplasmic tail. Selectins mediate cell-cell adhesion through interactions of the lectin domains with specific glycoconjugate ligands. The selectins bind with low affinity to the tetrasaccharide sialyl Lewis x ($sLe^x$; NeuAc$\alpha$2,3Gal$\beta$1,4[Fuc$\alpha$1,3]GlcNAc) and its isomer sialyl Lewis a ($sLe^a$; NeuAc$\alpha$2,3Gal$\beta$1,3[Fuc$\alpha$1,4]GlcNAc). P- and L-selectins, but not E-selectin, also bind to particular sulfated carbohydrates that lack sialic acid and fucose, such as heparan sulfate [4, 5, 7]. Selectins bind with higher affinity or avidity to only a few glycoproteins. Most are mucins, which are glycoproteins with multiple Ser/Thr-linked oligosaccharides (O-glycans) and repeating peptide motifs [4, 5]. Crystal structures of $sLe^x$ bound to the lectin domains of P- and E-selectin showed a network of interactions between fucose, a single $Ca^{2+}$ ion and several amino acids including those that coordinate the $Ca^{2+}$ [8]. The sialic acid and galactose also interact with the lectin domain. Targeted disruption of the gene encoding $\alpha$1,3 fucosyltransferase (Fuc-TVII) in mice significantly reduces selectin-mediated leukocyte trafficking. Disruption of the genes for both Fuc-TVII and Fuc-TIV completely eliminates these interactions [9, 10], indicating that all physiologically relevant selectin ligands require $\alpha$1,3-linked fucose.

PSGL-1 is the Specific Glycoprotein Ligand for P-Selectin on Leukocytes.

PSGL-1 (CD162) has been shown to be the specific ligand for P-selectin. Early studies using ligand blotting and affinity chromatography showed that P-selectin binds preferentially to a single glycoprotein in human myeloid cells [11]. The glycoprotein, (now known as P-selectin glycoprotein ligand-1, or PSGL-1), was shown to be a disulfide-bonded homodimer with two 120-kD subunits by SDS-PAGE under reducing and nonreducing conditions. Digestion with peptide N-glycosidase F demonstrated that PSGL-1 has at most two or three N-glycans that are not required for binding to P-selectin [11]. Treatment with sialidases indicated that $\alpha$2,3-linked sialic acid is required for P-selectin binding, indicating that PSGL-1 expresses functional sialylated O-glycans. The glycoprotein was found to contain the $sLe_x$ antigen and to have many sialylated, clustered O-glycans that render it susceptible to cleavage with O-sialoglycoprotein endopeptidase [12]. Treatment of intact myeloid cells with O-sialoglycoprotein endopeptidase eliminates the high-affinity binding sites for P-selectin without affecting overall surface expression of $sLe^x$ [12, 13]. Antibody blocking studies and genetic deletion of PSGL-1 demonstrate that PSGL-1 is the dominant ligand for P- and L-selectins on leukocytes. Studies with synthetic glycosulfopeptides which mimic the N-terminal domain of PSGL-1, indicated that P-selectin binds in a stereo-specific manner to the amino terminal of PSGL-1 through recognition of a tripartite domain containing tyrosine sulfate residues, adjacent peptide determinants, and fucose, galactose and sialic acid residues on a core-2 O-glycan [14, 15]. The crystal structure of P-selectin complexed with a glycosulfopeptide derived from PSGL-1 revealed a broad shallow binding interface [8]. The $Ca^{2+}$-dependent interactions with $sLe^x$ were augmented by $Ca^{2+}$-independent contacts with tyrosine sulfate and other amino acids. This explains why P-selectin binds with higher affinity to PSGL-1 than to $sLe^x$ alone.

The Primary Structure of PSGL-1.

A cDNA encoding PSGL-1 was isolated from a human HL-60 cell library by expression cloning using COS cells that were panned on immobilized P-selectin [16]. Functional expression of PSGL-1 in COS cells required cotransfection with an $\alpha$1,3 fucosyltransferase, and confirmed earlier observations that both $\alpha$1,3 fucosylation and $\alpha$2,3 sialylation of surface glycoproteins are required for binding to P-selectin [17]. The deduced amino acid sequence of PSGL-1 (SEQ ID NO:1) reveals a type 1 membrane protein of 402 amino acids. It has an $NH_2$-terminal signal peptide, a propeptide that is cleaved by paired basic amino acid converting enzymes. The extracellular domain of the mature protein begins at residue 42 and has the hallmarks of a mucin. It is rich in serines, threonines, and prolines, and includes 15 decameric repeats. Three $NH_2$-terminal tyrosines at residues 46, 48, and 51 are located in an anionic consensus sequence that favors tyrosine sulfation. There is a single extracellular cysteine located at the junction of the transmembrane domain, which is followed by a cytoplasmic domain of 69 residues. The cDNA for murine PSGL-1 reveals a protein of similar size to the human protein. Murine PSGL-1 also has a signal peptide, a propeptide, and a single cysteine near the transmembrane domain [18]. Furthermore, murine PSGL-1 has an anionic $NH_2$-terminal sequence with two rather than three tyrosines. The sequences of the murine and human transmembrane and cytoplasmic domains are highly conserved, implying important functions. The murine extracellular domain, although rich in serines, threonines, and prolines, has only 10 decameric repeats, and shares little sequence similarity with the human protein. A single exon encodes the open reading frame in both the human and murine PSGL-1 genes [18, 19]. The sequence of PSGL-1 in most human leukocytes has an additional decameric repeat not found in the protein from HL-60 cells and other cell lines [19, 20]. Human PSGL-1 is sulfated [21-23], but the sulfate is present exclusively on tyrosine residues rather than on O-glycans [24, 21]. Sulfation occurs on one or more of the three clustered tyrosines at residues 46, 48, and 51 of SEQ ID NO:1 [22, 23]. Enzymatic removal of sulfate [21], blockade of sulfate synthesis [22, 23], proteolytic removal of an NH2-terminal fragment containing the three clustered tyrosines [25], or replacement of the tyrosines with phenylalanines [22, 23, 26] eliminates binding of PSGL-1 to P-selectin. Other structural features of PSGL-1 may also be important for optimal binding to P-selectin. The acidic residues surrounding the tyrosines may favor binding, although they are not sufficient in the absence of tyrosine sulfate.

PSGL-1 Binding to L- and E-Selectins.

PSGL-1 has also been shown to bind to both L-selectin [27-29] and E-selectin [16, 30-32]. Binding of PSGL-1 to L-selectin is blocked by the mAb PL1 [27-29, 33], by enzymatic removal of the $NH_2$-terminal clustered tyrosines [29], or by the prevention of sulfate synthesis [29]. These results suggest that L- and P-selectins bind to a similar $NH_2$-terminal region of PSGL-1 that requires both tyrosine sulfate and O-glycan(s). L-selectin binds to a group of mucins expressed on lymph node high endothelial venules (HEVs) and on some activated endothelial cells. These mucins include CD34, GlycCAM-1 and podocalyxin. PSGL-1 binds much differently to E-selectin than to P- or L-selectin. Core-2, sialylated and fucosylated O-glycans are required for binding to E-selectin [34], but tyrosine sulfation is not required [22, 23, 34]. E-selectin also binds to the $NH_2$-terminal region of PSGL-1 [30, 35], although with lower affinity than does P-selectin [30]. The anti-PSGL-1 mAb PL1 has little or no effect on binding of PSGL-1 to E-selectin. This and other data indicate that E-selectin also binds to one or more still uncharacterized sites on PSGL-1 [35, 36]. Genetic deletion of PSGL-1 in mice impairs leukocyte tethering to E-selectin in vitro and in vivo [37]. Combined with the data on P- and L-selectin, this establishes that PSGL-1 is a physiologically relevant glycoprotein ligand for all three selectins.

The Tissue Distribution of PSGL-1.

Northern blot analysis indicated that mRNA for PSGL-1 is expressed in many human and murine organs, but did not indicate the specific cells in which it is expressed [16, 18]. Flow cytometric and immunocytochemical analysis of multiple human tissues with the anti-PSGL-1 mAbs PL1 or PL2 revealed that the PSGL-1 core protein is expressed primarily in hematopoietic cells [20, 38]. In bone marrow it is expressed on myeloid cells at many stages of maturation, but not on erythroid cells, megakaryocytes, or platelets. PSGL-1 is expressed on virtually all leukocytes, but at lower levels on B cells. P-selectin binds to PSGL-1 on all myeloid cells [20]. However, it binds to PSGL-1 on only a subset of T cells [20, 39]; most of these are memory cells [40] and they may be predominantly $\gamma/\delta$ cells [41]. PSGL-1 is expressed on circulating dendritic cells, on tissue monocyte derived dendritic cells, and on some dendritic cells in lymphoid organs; the function of the protein in these cells is unknown. PSGL-1 is also expressed on some $CD34^+$ stem cells [38], where it may bind P-selectin [42]. The PSGL-1 protein is also expressed on epithelial cells lining the fallopian tube and in some endothelial cells at sites of chronic inflammation [38] and in epithelial cells and lamina propria of intestinal mucosal lining [126]. It has been reported that P-selectin is present on the surface of porcine sperm, where it binds to a P-selectin ligand which may be related to PSGL-1, on the zona pellucida of porcine oocytes [43].

PSGL-1-Selectin Interactions Mediate Tethering and Rolling of Leukocytes Under Hydrodynamic Flow.

The functional significance of PSGL-1 interactions with the selectins has been identified. Under hydrodynamic flow, selectin-ligand interactions must form rapidly to facilitate tethering, and then dissociate rapidly to facilitate rolling. Selectin-ligand bonds must have mechanical strength so that shear forces do not significantly accelerate the rate of dissociation [1]. There are relatively few copies of PSGL-1 on leukocytes [13. 20], and PSGL-1 displays only a small fraction of the total $sLe^x$-containing glycans on the cell surface [12]. However, PSGL-1 is the only high affinity ligand for P-selectin on intact leukocytes [20], and PSGL-1 is the essential ligand for mediating adhesion of leukocytes to P-selectin. The anti-PSGL-1 mAb PL1 blocks tethering and rolling of human neutrophils, eosinophils, and mononuclear cells on P-selectin under flow [20, 44]. PL1 also abrogates adhesion of neutrophils and monocytes to P-selectin under static conditions [20, 45, 46]. The PL1 mAb to an $NH_2$-terminal epitope of murine PSGL-1 has been shown to block tethering and rolling of murine myeloid cells on P-selectin under flow [47]. Thus, interactions of PSGL-1 with P-selectin mediate adhesion of leukocytes to both activated endothelial cells and platelets under shear stress. The requirement for PSGL-1 to mediate leukocyte adhesion to P-selectin probably reflects, in part, its superior binding affinity relative to other ligands. The orientations of both PSGL-1 and P-selectin on the cell surface may also optimize their interactions under hydrodynamic flow. Both P-selectin and PSGL-1 are highly extended proteins, which project their $NH_2$-terminal binding domains above most of the cell surface glycocalyx [13, 26]. Most of the O-glycans on PSGL-1 may function primarily to extend the $NH_2$-terminal region above the plasma membrane. When expressed on transfected CHO cells, shortened P-selectin constructs with fewer short consensus repeats are much less effective than wild-type P-selectin in mediating tethering and rolling of neutrophils under flow [36]. PSGL-1 is also concentrated on microvillous tips [20, 48]. Thus, both the lengths and surface distributions of PSGL-1 and P-selectin may enhance rapid and specific interactions, yet minimize nonspecific repulsion between apposing cell surfaces. Upon neutrophil activation, PSGL-1 undergoes a cytoskeletal-dependent redistribution to the uropods of polarized cells [48-50]. This redistribution is associated with weakening of adhesion to P-selectin and transfer of adhesive control to integrins [49, 50]. Like PSGL-1, L-selectin is also concentrated on the tips of microvilli [51]. Leukocytes use L-selectin to roll on adherent leukocytes [52] or to initiate leukocyte aggregation [53]. Leukocyte-leukocyte interactions lead to secondary tethering of leukocytes to a P- or E-selectin surface, a potential mechanism for amplifying leukocyte recruitment to the vessel wall under shear forces [27, 54]. Flowing leukocytes roll on purified PSGL-1; this interaction is blocked by PL1 and by mAbs to L-selectin [27]. Furthermore, PL1 significantly inhibits the L-selectin-dependent rolling of neutrophils on adherent neutrophils [27] and the L-selectin-dependent aggregation of stirred neutrophils [33]. These data suggest that PSGL-1 is an important ligand for L-selectin under at least some conditions. However, there are L-selectin ligands other than PSGL-1 that participate in leukocyte-leukocyte contacts [27, 54, 55]. PSGL-1 may be one of only a few glycoproteins in human leukocyte lysates that binds well to E-selectin [31, 56]. Microspheres coated with recombinant PSGL-1 also roll on immobilized E-selectin under shear forces [35]. However, it is not clear whether PSGL-1 has any significant function for adhesion of leukocytes to E-selectin and this remains to be demonstrated. PL1 partially reduces accumulation of rolling neutrophils on E-selectin under flow [36]. But this effect occurs indirectly through inhibition of L-selectin-PSGL-1 interactions between neutrophils, thus reducing secondary tethering of neutrophils to E-selectin [36]. PL1 blocks primary tethering of flowing leukocytes to P-selectin but not to E-selectin [36, 54]. Human K562 cells transfected with FTVII roll on E-selectin in the absence of PSGL-1 [57]. Conversely, eosinophils, which express PSGL-1 but express relatively little total sLe$^x$, tether and roll much less efficiently on E-selectin than on P-selectin [44, 58]. Together, these data suggest that E-selectin must bind to ligands other than PSGL-1 to mediate leukocyte attachment under flow.

Signaling Through PSGL-1.

In the multistep model of leukocyte recruitment, leukocytes rolling on endothelial cells or platelets encounter regionally presented chemokines and lipid autacoids that stimulate the leukocytes to develop integrin-dependent firm adhesion and other responses. However, signals may also be directly transmitted through adhesion molecules [3]. The available data suggest that binding of P-selectin to PSGL-1 on leukocytes generates signals that must be integrated with those from other activators to elicit most effector responses [3]. In the best studied examples, monocytes mobilize the transcription factor NFκB and synthesize the cytokines TNFα and monocyte chemotactic protein-1 (MCP-1) when the cells adhere to immobilized P-selectin and platelet-activating factor, but not to either molecule alone [45]. Monocytes secrete a different profile of cytokines when they are exposed to P-selectin and the platelet derived chemokine, RANTES, but not to either protein alone [46]. Under some conditions, cooperative signaling through PSGL-1 and receptors for conventional activators may also generate other leukocyte responses [3, 59]. Adhesion of T cells to P-selectin was reported to induce tyrosine phosphorylation of the pp125 focal adhesion kinase (FAK), although the role of PSGL-1 in this event was not directly tested [60]. pp125 FAK has not been detected in human myeloid cells [61]. However, engagement of PSGL-1 with bivalent mAbs or immobilized P-selectin induces rapid tyrosine phosphorylation of other proteins in human neutrophils [62]. These include the ERK family of mitogen-activated protein kinases, which are activated by PSGL-1 engagement. Engagement of PSGL-1 with mAbs is sufficient to stimulate neutrophils to secrete IL-8. This secretion is blocked by a tyrosine kinase inhibitor, suggesting that tyrosine phosphorylation propagated through PSGL-1 may be physiologically important [62]. Cross-linking of L-selectin also rapidly transmits signals into both myeloid and lymphoid cells [63-68]. Thus, binding of L-selectin to PSGL-1 during leukocyte-leukocyte interactions may transmit bidirectional, potentially cooperative, signals during the earliest phases of leukocyte recruitment.

Physiological and Pathological Functions of PSGL-1-Selectin Interactions.

Recent in vivo studies have confirmed the predictions from in vitro experiments that PSGL-1 is a physiologically important selectin ligand. Anti-PSGL-1 mAbs inhibit rolling of both human and murine leukocytes on P-selectin expressed in postcapillary venules in vivo [47-69]. Polyclonal antibodies directed to the NH$_2$-terminal segment of murine PSGL-1 specifically inhibit the recruitment of T helper 1 lymphocytes in a delayed-type hypersensitivity model [47]. A mAb to the NH$_2$-terminal region of murine PSGL-1 also inhibits accumulation of neutrophils into chemically inflamed peritoneum [47]. The degree of inhibition is comparable to that observed with a mAb to P-selectin. More complete inhibition is observed with the combined use of mAbs to both PSGL-1 and P-selectin, suggesting that PSGL-1 interacts with at least one other molecule. An obvious candidate is L-selectin, given the in vitro evidence that binding of L-selectin to PSGL-1 mediates leukocyte-leukocyte interactions. Since PSGL-1 promotes adhesive interactions through both P- and L-selectins, it is almost certain to contribute to pathological leukocyte recruitment in a variety of inflammatory and thrombotic disorders in which P- and L-selectins have been implicated previously [6]. This suggests that mAbs to PSGL-1, soluble forms of PSGL-1, and other inhibitors of PSGL-1 function are potentially useful anti-inflammatory drugs in such conditions. In support of this concept, infusion of recombinant soluble PSGL-1 potently inhibits leukocyte infiltration and parenchymal damage in rat kidneys subjected to ischemia and reperfusion. Proteolytic removal of the NH$_2$-terminal region of PSGL-1 abrogates its protective effects [70]. This implies that soluble PSGL-1 blocks adhesion of leukocytes to P-selectin and perhaps to L-selectin in this model. In other pathological states, soluble PSGL-1 may also be an effective E-selectin inhibitor even if PSGL-1 on leukocyte surfaces is not a dominant ligand for E-selectin. Use of a mAb blocking P- and E-selectin may not be supported by data in double P/E$^{-/-}$ knock out mice that showed increased susceptibility to infection an altered hematopoiesis [71].

Development of Anti-PSGL-1 Antibodies and Characterization of their Binding Epitopes on PSGL-1.

Several function-blocking mouse monoclonal antibodies to human PSGL-1 have been developed. A mouse monoclonal antibody named PL1 was developed using standard hybridoma technology by immunization of mice with PSGL-1 from human neutrophils [34]. PL1 was shown to bind a 14 amino acid epitope encompassing residues 49-62 of the native human protein (SEQ ID NO:1) using linear epitope mapping with overlapping octamer peptides spanning residues 19-77 of PSGL-1. PL1 was shown to block leukocyte adhesion to P-selectin in static adhesion assays and under flow [20]. Another anti-human-PSGL-1 antibody named KPL-1 was developed by immunization of mice with a recombinant form of PSGL-1. KPL1 inhibited interactions between P-selectin and purified CD4 T cells and neutrophils in flow assays, between lymphoid cells transfected with L-selectin and COS cells expressing PSGL-1, but did not block interactions of P-selectin or neutrophils on E-selectin [72]. KPL1 was subsequently shown to bind to a 17mer synthetic peptide encompassed by the binding domain of PL1 [73]. Another antibody, termed RR2r3s4-1, was engineered as a fully human antibody from a single chain Fv which had been isolated from a pool of PSGL-1 binders identified from a yeast surface display non-immune library [74, 125]. RR2r3s4-1 blocked neutrophil adhesion under flow and was shown to be specific for human, but not murine, PSGL-1.

Recent studies have also shown that PSGL-1 plays a dual function role in that along with its binding of selectins, PSGL-1 also interacts with chemokines to facilitate homing of T cells to secondary lymphoid organs [75-76].

Chemokines.

Chemokines are highly basic proteins consisting of 70-125 amino acids with molecular masses ranging from 6-14 kD [77, 78]. To date over 50 chemokines have been identified. The superfamily of chemokines is subclassified on the basis of the arrangement of cysteine residues located in the N-terminal region, as designated C, CC, CXC, and CX3C members, in which C represents the number of cysteine residues in the N-terminal region and X denotes the number of intervening amino acids in between the first two cysteines [77, 79, 80]. The CXC subfamily is sometimes further classified into ELR+ and ELR types based on the presence or absence of a triplet amino acid motif (Glu-Leu-Arg) that precedes the first cysteine residue in the primary amino acid sequences of these chemokines. The presence of this motif imparts an angiogenic function to this subset of CXC chemokines, while the ELR-chemokines have angiostatic properties [81], with the exception of SDF-1 which is angiogenic [82]. In general, the chemokines attract distinct classes of leukocytes: CC chemokines attract one or more classes of mononuclear cells, eosinophils and basophils; ELR+CXC chemokines attract neutrophils; ELR–CXC chemokines attract lymphocytes; C chemokine (lymphotactin) attracts T cells and CX3C chemokine (fractalkine) acts on T cells, natural killer cells and monocytes [83]. Chemokines are produced by a variety of cell types either constitutively or in response to inflammatory stimuli. Chemokines can be broadly divided into homeostatic and inflammatory categories based on their expression pattern and function in the immune system [78, 80]. The homeostatic chemokines are generally those that are "constitutively" expressed. They are involved in homeostatic lymphocyte and dendritic cell (DC) trafficking and lymphoid tissue organogenesis. The "inflammatory" chemokines are upregulated by proinflammatory stimuli and help orchestrate innate and adaptive immune responses. Although most chemokines are present in soluble forms and some may be associated with glucosaminoglycan moieties on the cell surface, two of the chemokines namely CX3CL1 (fractalkine) and CXCL16, have a natural mucin stalk that adheres onto the membrane of the cells that produce them [84, 85]. Their "chemokine" domain is located at the N-terminus of the mucin stalk and can be released by metalloproteinase cleavage. While the soluble, released chemokine domain of CX3CL1 and CXCL16 functions similarly to other secreted chemokines, their membrane bound forms play an important role in mediating leukocyte-endothelial cell adhesion and extravasation. Chemokines exert their biological effects by binding to G protein-coupled cell surface receptors. Nineteen chemokine receptors have been cloned so far [80, 86], including six CXC receptors (CXCR1-6), eleven CC receptors (CCR1-11), one CX3C (CX3CR1) and one C receptor (XCR1). Chemokine and receptor interactions vary widely in terms of selectivity. Some chemokines bind only one receptor and vice versa, such as the interactions of CXCR4 with CXCL12 (SDF-1), CXCR5 with CXCL13 (BCA-1), CXCR6 with CXCL16, CCR6 with CCL20 (LARC), and CCR9 with CCL25 (TECK). However, there is also redundancy in chemokine and receptor interactions since some chemokines bind more than one receptor and many receptors recognize more than one chemokine. For example, chemokine CCL5 (RANTES) has been shown to bind at least CCR1, CCR3 and CCR5, while CCR3 also binds CXCL11 (eotaxin), CCL24 (eotaxin-2), CCL26 (eotaxin-3), CCL8 (MCP-2), CCL7 (MCP-3), and CCL13 (MCP-4). Furthermore, two of the chemokine receptor-like proteins, the Duffy antigen receptor for chemokines (DARC) and D6, promiscuously bind many of the CXC and CC chemokines with equal affinity [87-89], but without being activated, presumably acting as sinks that sequester inflammatory chemokines.

Leukocyte Trafficking and Homing.

Chemokines control lymphocyte recirculation in immune system homeostasis, as well as in the activation dependent and tissue-selective trafficking of effector and memory lymphocytes. Lymphocyte homing to lymphoid and nonlymphoid tissues and recirculation between secondary lymphoid organs critically depend on the chemokines present in different sites. CCL19 and CCL21 (which bind to CCR7), and CXCL13 (which binds to CXCR5), are expressed in the lymphatic vessels, high endothelial venules (HEVs) and secondary lymphoid organs, and promote the entry of antigen-presenting cells (APCs), T cells and B cells into these organs [90]. Resident DC precursors in peripheral tissues phagocytose microorganisms or cell debris and are activated by pathogens or antigens. These cells then start to mature and express CCR7 which enables them to migrate in response to CCR7 ligands into the draining lymph nodes via the lymphatic vessels, and to infiltrate the T-cell zones where they present processed antigen epitopes to T cells. In contrast to DCs, B cells and naïve T cells enter lymph nodes through HEVs. The CCR7 ligands CCL19 and CCL21 produced by the endothelial cells of HEVs are transcytosed to the luminal surface and induce lymphocyte extravasation to the T-cell zones of the lymph nodes [91]. CCL19 produced by mature, inter-digitating DCs facilitates the "scanning" of DCs by naïve T cells in the lymphoid organs in search of their cognate antigens. B cells express CXCR5 and the ligand CXCL13 is produced by follicular stromal cells in lymph nodes. B cells activated by T cells proliferate in the follicles, giving rise to germinal centers (GC). Activated T cells expressing CXCR5 may also enter the follicles to participate in the T-B interaction. In addition, CCL19 and CCL21 are responsible for the proper positioning of lymphocytes within distinct microenvironments of lymphoid organs. For instance, CCL19 and CCL21, expressed by DCs and stromal cells retain T cells within the T-cell zones of secondary lymphoid organs. On the other hand, CXCL13 expressed by follicular DCs and stromal cells in follicles attracts B cells and some of the T cell subsets into the B-cell areas. Furthermore, the capacity of B cells to respond to CCR7 as well as CXCR5 ligands controls the position of B cells at the boundary of the follicles and T-cell zones in the spleen, where naïve, mature B cells interact with T cells that are newly activated in the adjacent zones [92, 93]. Non-activated B cells and T cells then leave the secondary lymphoid organs via the efferent lymphatics.

Inflammation.

A central feature of inflammatory diseases is the migration of leukocytes from the circulation, across the endothelium and the basement membrane, and into the affected tissue. The mechanism of extravasation is induced by chemokines (chemoattractant cytokines), which as noted above are a family of proinflammatory mediators produced at the inflammatory site. As part of the migration process, circulating leukocytes must first adhere to the luminal surface of the endothelium. According to the current paradigm, this interaction involves the sequential engagement of leukocyte and endothelial adhesion molecules. First, selectins and their glycoprotein and carbohydrate counterligands mediate leukocyte tethering and rolling. Then, leukocyte integrins and their ligands, including immunoglobulin-like intercellular adhesion molecules, mediate firm leukocyte adhesion. Chemokines play a role in firm adhesion by activating integrins on the leukocyte cell surface. The leukocytes are directed by chemoattractant gradients to migrate across the endothelium, and through the extracellular matrix into the tissue.

The events that lead to an inflammatory response are characterized by recognition of the site of injury by inflammatory cells, recruitment of specific leukocyte subpopulations, removal of offending microbial invaders, "debridement" of injured cells/tissues, and wound repair. Chemokines have been shown to participate in and control the process of a number of acute and chronic inflammatory conditions by promoting the infiltration and activation of inflammatory cells into injured or infected tissues [94].

Several of the CC chemokines including CCL3 (MIP-1α) and CCL5 (RANTES) are expressed in sepsis and exert proinflammatory effects by mediating organ specific leukocyte influx and activation [95, 96]. Members of the CXC chemokines are implicated in the pathogenesis of systemic inflammatory response [97, 98]. In bacterial pneumonia, CXC chemokine-mediated elicitation of neutrophils is beneficial and necessary for clearance of invading microorganisms [98]. To support this notion, over expression of KC, a murine homologue of human CXCL1 (GRO-α), specifically in the lung, enhances resistance to *Klebsiella* pneumonia [99]. In asthma, the submucosa of small airways is infiltrated by mononuclear, eosinophil and mast cells causing mucous gland hyperplasia and subepithelial fibrosis. Animal models of allergic airway inflammation and asthmatic patients imply a key role for chemokines in regulating lung inflammation [100]. The kinetics of production of CCL2, CCL11, CCL17 and CCL22 correlates with the recruitment in airways of specific leukocyte subsets expressing the receptors for these chemokines [101]. Chronic obstructive pulmonary disease (COPD) is characterized by progressive development of airflow limitation caused by chronic inflammation with increased recruitment of neutrophils, macrophages and IFN-γ-producing CD8+ T cells in the lung. In COPD patients, the levels of CXCL8 and CXCL10 are increased and correlate with the degree of infiltration by neutrophils and CD8+ T cells that produce IFN-γ. The lung-infiltrating T cells express CXCR3, the receptor for CXCL10 [102], suggesting that CXCR3 may mediate the recruitment of pathogenic Th1 cells into chronically inflamed lungs. Neutralization of CXCL10 also appears to inhibit allergic airway inflammation [103]. Thus, in addition to many other chemokines, CXCR3 and its ligands participate in lung inflammation that is not necessarily dominated by Th1 response. Atherosclerosis is widely accepted as an inflammatory disease [104], in which chemokines play a central role in leukocyte recruitment, angiogenesis, and more intriguingly in the proliferation of vascular smooth muscle cells and their migration into plaques [105]. Atherosclerotic lesions express a number of chemokines including CCL2, CCL3, CCL4, CCL5, CCL11 and CXCL8. The cellular sources of chemokines within atherosclerotic lesion are multiple and include endothelial cells, smooth muscle cells and infiltrating leukocytes. There is overwhelming evidence to support the involvement of CCL2/CCR2 chemokine-receptor pair in atherosclerosis. CCL2 is essential for monocyte recruitment, has angiogenic activity and also causes smooth muscle cell proliferation and migration. Many factors known to promote atherosclerosis such as plasma cholesterol, hypertension and diabetes, stimulate chemokine release by atheromatous lesions. Adhesion of leukocytes to endothelial cells also augments chemokine release in the pathogenic process of atherosclerosis. Therefore, chemokines and receptors become important molecular targets for circumventing the formation and development of atherosclerotic lesions. In human, CX3CR1 gene polymorphism in the coding region confers individuals with protection against atherosclerosis [106, 107]. An M280 mutation in CX3CR1 results in loss of function of CX3CR1 since cells transfected with this mutant receptor exhibit a markedly reduced response to CX3CR1 ligand CX3CL1 [108]. When ApoE transgenic mice, an atherosclerosis model, were crossed with CX3CR1-/- mice, the severity of atherosclerotic lesion was significantly reduced with lower macrophage infiltration. This provides an excellent example of the importance of a functional chemokine receptor in contributing to the progression of atherosclerosis. Rheumatoid arthritis (RA) is characterized by a mixed Th1-type inflammatory cell infiltration (Th1 cells, neutrophils, monocytes) in synovial space of the joints [109], in association with cartilage destruction and bone remodeling. Chemokines produced in the inflamed joints attract leukocytes across the endothelial barrier to initiate and maintain active RA [110, 111]. Among CXC chemokines, high concentrations of CXCL8, CXCL5, CXCL1 are detected in the sera, synovial fluids, and synovial tissues of RA patients [109, 110]. These chemokines attract neutrophils and promote angiogenesis [109, 110]. Abundant production of CC chemokines CCL2, CCL3 and CCL5 which attract mainly monocytes is also found in RA [109, 110]. On the other hand, CXCL12 expressed in the rheumatoid synovium, recruits CD4 memory T cells, which express increased levels of CXCR4, at the RA site [111]. CXCL12 also blocks T cells from undergoing activation-induced apoptosis, thus further increasing the accumulation of T cells in the rheumatoid synovium. Interestingly, CXCL12 may induce the migration of DCs from blood stream into the rheumatoid area, implying its potential role in amplifying a detrimental autoimmune response. Multiple sclerosis (MS) as a chronic inflammatory demyelinating disorder of the central nervous system (CNS) is thought to be caused by an autoimmune response directed against self-myelin-associated antigens. The immune cells infiltrate in CNS lesions of MS patients consist of CD4, CD8 T cells and macrophages [112]. Many chemokines are detected in active lesions in the CNS of MS patients and the cerebrospinal fluids of relapsing patients contain elevated levels of CCL3 [113, 114]. In MS, infiltrating macrophages express CCR2 and CCR5, while T cells and reactive astrocytes in active lesions express CXCR3 and CCR5 [115, 116]. Similar chemokine expression patterns are found in experimental autoimmune encephalomyelitis (EAE), an animal model more related to MS. In EAE, increased expression of CCL2, CCL3, CCL4, CCL5 and CXCL10 correlates with the severity of the disease ([117]). Neutralizing antibodies to selected chemokines either inhibit the onset or reduce the severity of the EAE [118, 119]. A more definitive correlation between chemokines and EAE was established by experiments with CCR1- and CCR2-deficient mice, in which a reduction in disease incidence and severity were clearly documented [120, 121]. A link between chemokines and Crohn's Disease has also been established. The expression of chemokines CCL-19 and CCL-21 have been shown to be upregulated in the colon tissue, secondary lymphoid tissue and mesenteric lymph nodes derived from patients with Crohns disease [122, 123]. Further, the CCR7 receptor is also upregulated on dendritic cells in the colonic tissue of these patients which interact with T cells resulting in activation and proliferation. This increased expression of chemokines and chemokine receptors leads to increased retention of dendritic cells in colon tissue resulting in the formation of tertiary lymphoid tissue formation in the bowel wall which maintains the autoimmune inflammation in Crohn's disease [122, 123].

Clearly, the development of human- (and primate-) compatible monoclonal antibodies which block the chemokine mediated migration of leukocytes into, and their P-selectin mediated adhesion and rolling to cells in areas of inflammation and which have reduced immunogenicity would be of great value.

SUMMARY OF THE INVENTION

The present invention is directed to purified antibodies (including chimeric, human, or humanized antibodies) and antigen binding fragments thereof, which recognize (i.e., bind to) P-selectin glycoprotein ligand-1 (PSGL-1) and which block binding of both P- and L-selectin and chemokines thereto, and to methods for screening for such antibodies and antigen binding fragments thereof, and to methods of therapeutic use thereof.

The antibodies or antibody fragments of the present invention may comprise immunoglobulin of the class $IgG_1$, $IgG_2$, $IgG_3$, $IgG_4$ or is an $IgG_2/G_4$ chimera, preferably binds to PSGL-1 with a high affinity (wherein the $K_d$ is $\leq$100 nM) and preferably comprises a human constant region, and preferably competitively inhibits binding of P-selectin and/or L-selectin to PSGL-1 and competitively inhibits binding of a chemokine to PSGL-1. Further, the anti-PSGL-1 antibody or antigen binding fragment thereof preferably does not activate complement via the classical pathway by interacting with C1Q, and preferably does not bind Fc receptors. The present invention in particular is directed to using such anti-PSGL-1 antibodies or antibody fragments as described and identified herein in treatments for inflammatory conditions wherein the inflammation is associated with a condition such as, but not limited to, at least one of: inflammatory bowel disease (e.g., Crohn's disease, ulcerative colitis, enteritis), arthritis (e.g., rheumatoid arthritis, osteoarthritis, psoriatic arthritis), graft rejection, graft versus host disease, asthma, chronic obstructive pulmonary disease, psoriasis, dermatitis, nephritis, lupus erythematosis, scleroderma, rhinitis, anaphylaxis, diabetes, multiple sclerosis, atherosclerosis, thrombosis, allergic reactions, and thyroiditis.

BRIEF DESCRIPTION OF THE DRAWINGS

FIG. 1 shows amino acids 42-62 of SEQ ID NO:1 (PSGL-1) and portions thereof which encompasses a chemokine binding epitope to which the antibodies PL1, KPL1, and SelK1 bind.

FIG. 8 (A, B) shows the positions of the signal peptide, VH chain, hinge portion, and CH1, CH2, and CH3 chains in the amino acid sequence (SEQ ID NO:2) and corresponding encoding nucleic acid sequence (SEQ ID NO:3) of the heavy chain of the SelK1 antibody.

FIG. 9 shows the positions of the signal peptide, VL chain and CL chain, in the amino acid sequence (SEQ ID NO:4) and corresponding encoding nucleic acid sequence (SEQ ID NO:5) of the light chain of the SelK1 antibody.

DETAILED DESCRIPTION OF THE INVENTION

Figure 2:
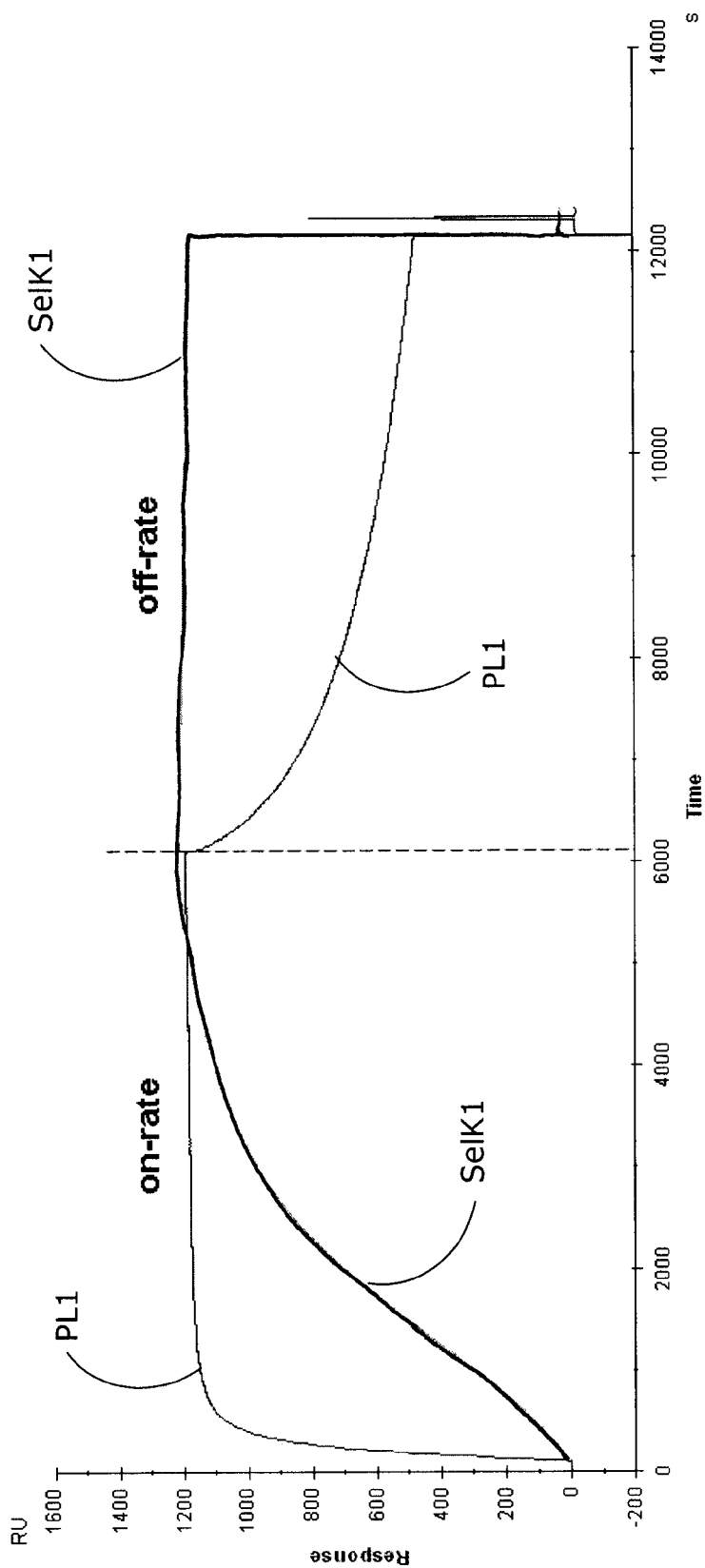
FIG. 2 shows a graph of Surface Plasmon Resonance analysis of on- and off-rates for PL1 and SelK1 anti-PSGL-1 antibodies. Binding of the human anti-PSGL-1 antibody (SelK1) and PL1 were analyzed at 25 nM to human PSGL-1 covalently bound to a BIACORE chip for 100 min. at which time buffer lacking antibody was introduced. PL1 exhibited fast on/off kinetics to PSGL-1. SelK1 had a very slow on-rate and a nearly undetectable off rate indicating the high affinity of the antibody for PSGL-1.

The present invention is directed to purified antibodies (including chimeric, human, or humanized antibodies) and antigen binding fragments thereof, which recognize (i.e., bind to) P-selectin glycoprotein ligand-1 (PSGL-1) and which block binding of both P-selectin and L-selectin and chemokines thereto, and to methods for screening for such antibodies and antigen binding fragments thereof, and to methods of therapeutic use thereof.

More particularly, the invention is directed to purified antibodies (or fragments thereof, against PSGL-1, host cells that produce such anti-PSGL-1 antibodies (or fragments thereof), screening assays to identify anti-PSGL-1 antibodies (or fragments thereof) which have a dual function in blocking leukocytes, lymphocyte and endothelial cell selectin-mediated adhesion and chemokine-mediated chemotaxis and therapeutic methods using such antibodies (or antigen binding fragments thereof). The present disclosure provides novel antibodies against primate (including human) PSGL-1 and antigen-binding fragments thereof, particularly including SelK1 antibody. Preferred antibodies of the invention are capable of specifically binding primate (particularly human) PSGL-1, and inhibiting one or more PSGL-1 activities in vitro and/or in vivo.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain.

Depending on the amino acid sequences of the constant domain of their heavy chains, immunoglobulins can be assigned to different classes. There are at least five major classes of immunoglobulins: IgA, IgD, IgE, IgG and IgM, and several of these may be further divided into subclasses (isotypes), e.g. $IgG_1$, $IgG_2$, $IgG_3$ and $IgG_4$ and $IgA_1$ and $IgA_2$. The constant domains of the heavy chains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments per chain called complementarity determining regions (CDRs), also known as hypervariable regions, both in the light chain and the heavy chain variable domains. As explained further below, in one embodiment of SelK1, an antibody of the present invention, the three CDRs of the variable heavy chain (CDRH1, CDRH2, and CDRH3) are SEQ ID NO:6-8, respectively. Similarly, in one embodiment of SelK1, the three CDRs of the variable light chain (CDRL1, CDRL2, and CDRL3) are SEQ ID NO:9-11, respectively.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each light and heavy chain are held together in close proximity by the FR regions and contribute to the formation of the antigen-binding site of the antibody. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDRs), and the like forms, all of which fall under the broad term "antibody", as used herein. In preferred embodiments, in the context of both the therapeutic and screening methods described below, an antibody or fragment thereof is used that is immuno-specific for an antigen or epitope of the invention as contemplated herein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from anti-body fragments. As used herein, "functional fragment" with respect to antibodies, refers to Fv, F(ab) and F(ab')$_2$ fragments.

Antibody fragments may be as small as about 4, 5, 6, 7, 8, 9, 10, 11, 12, 13, 14, 15, 16, 17, 18, 19, 20, 21, 22, 23, 24, 25, 26, 27, 28, 29, or 30, 35, 40, 45 or 50 or more amino acids. In general, an antibody fragment of the invention can have any upper size limit so long as it is has similar or immunological properties relative to antibody that binds with specificity to an epitope located within amino acids 42 or 62 of SEQ ID NO:1 and which blocks binding of P- and/or L-selectins and at least one chemokine thereto.

As noted elsewhere herein, antibody fragments contemplated herein retain some ability to selectively bind to all of or a portion of the PSGL-1 amino acid binding epitope described herein. Specifically, an antibody or antigen binding fragment of an antibody of the present invention is capable of binding to an epitope comprising one or more amino acid residues of a sequence comprising amino acid residues 42 to 62 of the sequence set forth in SEQ ID NO:1. Some types of antibody fragments are defined as follows:

Fab is the fragment that contains a monovalent antigen-binding fragment of an antibody molecule. A Fab fragment can be produced by digestion of whole antibody with the enzyme papain to yield an intact light chain and a portion of one heavy chain.

Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(Fab')$_2$ is the fragment of an antibody that can be obtained by treating whole antibody with the enzyme pepsin without subsequent reduction. F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association (VH-VL dimer). It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

A single chain antibody (SCA) is defined herein as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding.

The antibodies or antibody fragments of the present invention may comprise immunoglobulin of the class $IgG_1$, $IgG_2$, $IgG_3$, $IgG_4$ or $IgG_2/G_4$ chimeras, preferably binds to PSGL-1 with a high affinity (for example wherein the $K_d$ is ≦100 nM) and preferably comprises a human constant region, and preferably competitively inhibits binding of P-selectin and/or L-selectin to PSGL-1 and competitively inhibits binding of a chemokine to PSGL-1. Further, the anti-PSGL-1 antibody or antigen binding fragment thereof preferably does not activate complement via the classical pathway by interacting with C1Q, and preferably does not express effector function, and preferably does not bind Fc receptors. The present invention in particular is directed to using such anti-PSGL-1 antibodies or antibody fragments as described and identified herein in treatments for inflammatory conditions wherein the inflammation is associated with (but not limited to) at least one of inflammatory bowel disease (e.g., Crohn's disease, ulcerative colitis, enteritis), arthritis (e.g., rheumatoid arthritis, osteoarthritis, psoriatic arthritis), graft rejection, graft versus host disease, asthma, chronic obstructive pulmonary disease, psoriasis, dermatitis, nephritis, lupus erythematosis, scleroderma, rhinitis, anaphylaxis, diabetes, multiple sclerosis, atherosclerosis, thrombosis, allergic reactions, and thyroiditis.

As noted above, PSGL-1 plays a central role in recruitment of leukocytes and lymphocytes to inflammatory and thrombotic sites by binding to structurally related selectin receptors identified as P-, L- and E-selectin. PSGL-1 is constitutively expressed on leukocytes, including neutrophils and monocytes, and on some endothelial cells. Chemokines, as noted above, are responsible for homing and firm adhesion of leukocytes and lymphocytes through activation of integrins. In addition to its role in leukocyte adhesion, recent studies (discussed above) have shown that PSGL-1 interacts with chemokines through tyrosine sulfate motifs on its N-terminal domain.

The binding of the known antibodies PL1 and KPL1 to PSGL-1 is independent of sulfation of the tyrosines of the N-terminal domain of PSGL-1 and have been characterized and shown to overlap the region distal to the propeptide at residues 42-62 of PSGL-1 (FIG. 1). These residues also encompass a chemokine-binding epitope at residues 46-53 which contains three sulfated tyrosine residues which are essential for the chemokine binding thereto.

As noted above, RR2r3s4-1 ("RR"), an anti-human PSGL-1 antibody which was previously derived from a fully human IgG1 antibody to human PSGL-1 that was developed from a single-chain Fvs antibody isolated from a yeast display library [74, 124, 125]. The RR antibody was shown by tryptophan fluorescence quenching titration to have a $K_d$ of 1 nM. In vitro assays demonstrated that RR binds human neutrophils and in rolling assays RR was shown to inhibit human neutrophils rolling on P-selectin at a concentration of 3.3 nM. In competition assays RR was shown to be specific for human PSGL-1 and does not bind murine PSGL-1.

In the present invention portions of the light and heavy variable regions of RR were re-engineered by linking them to the hinge region of a consensus human $IgG_2$ constant domain and incorporated single amino acid substitutions to inactivate complement binding. The resulting anti-human PSGL-1 antibody is referred to herein as SelK1.

SelK1 antibody was tested for binding to GSP-6, a glycosylated, sulfated 18 amino acid peptide mimetic of amino acids 42-60 of SEQ ID NO:1 (the exposed N-terminus of PSGL-1) [14] using surface plasmon resonance (BIACORE). GSP-6 and its derivatives GSP-1 and GP-1 (discussed in more detail below) are shown in FIG. 1A-1B and FIG. 3A (GSP-1) of U.S. Pat. No. 7,223,845. Its kinetics were compared to another anti-PSGL-1 antibody called PL1 [20]. SelK1 antibody bound to GSP-6 with a much slower on-rate than PL1 and almost no detectable off-rate (FIG. 2). These characteristics are consistent with chronic administration for therapeutic use of this antibody to treat Crohn's Disease and other inflammatory-related diseases as described elsewhere herein.

Figure 3:
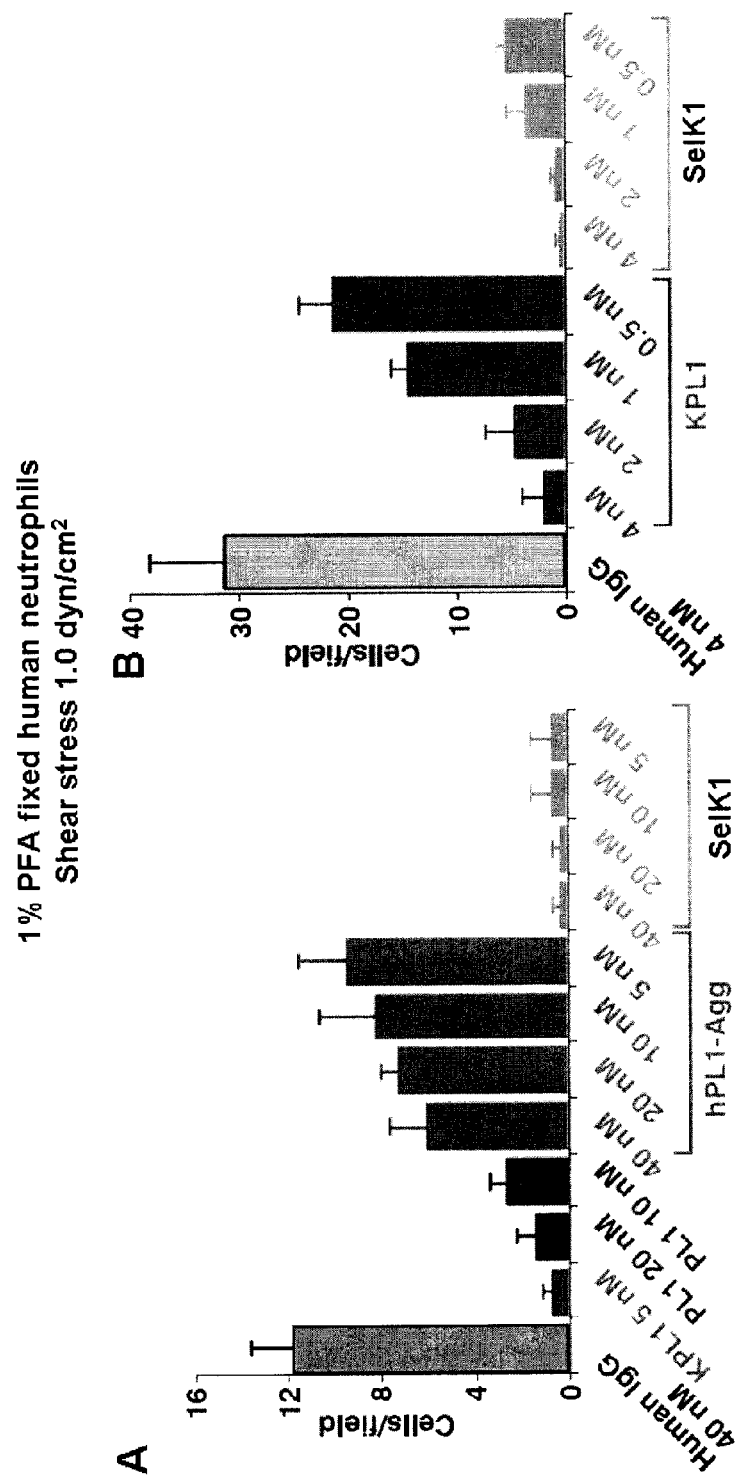
FIG. 3 (A, B) shows a table of flow inhibition analysis of anti-PSGL-1 antibodies. Human P-selectin was coated onto a chip at densities similar to activated endothelial cells and fixed human neutrophils introduced under flow stress that simulates blood flow with or without anti-PSGL-1 antibodies. Of the anti-PSGL-1 antibodies tested (KPL1, PK1, hPL1-Agg, and SelK1 anti-PSGL-1 antibody), SelK1 inhibited at the lowest concentration in blocking substantially 100% of neutrophil adhesion at 2 nM concentration.

SelK1 antibody was then tested for its ability to block neutrophil rolling on P-selectin in an in vitro rolling assay. In this assay fixed human neutrophils roll and tether to P-selectin coated on a plate to a density similar to that found on activated endothelial cells under flow simulating sheer stress in blood vessels [20]. When SelK1 was introduced into the flow at concentrations ranging from 40 nM to 2 nM, neutrophil rolling and tethering was completely blocked (FIG. 3). SelK1 was also compared to the mouse monoclonal anti-PSGL-1 antibodies PL1 and KPL1, and to a humanized PL1 termed hPL1-Agg. The results show that SelK1 was the most effective anti-PSGL-1 antibody of those tested in blocking neutrophil adhesion in this assay.

Figure 4:
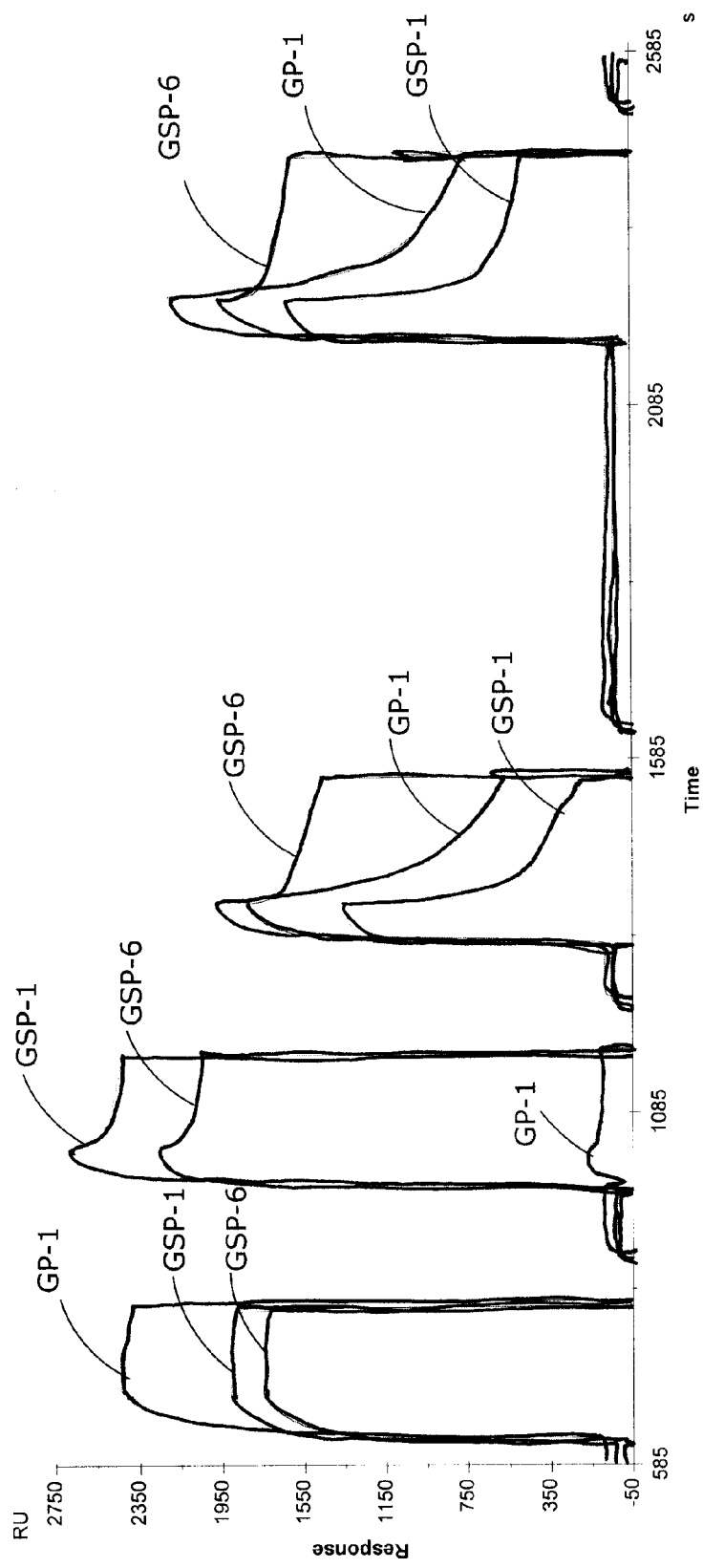
FIG. 4 shows a graph of the relative binding of antibodies KPL1, SelK1, hPL1 and PL1 to bound GP1, GSP-1, and GSP-6 peptides.

SelK1 antibody was tested for its ability to bind with specificity to GSP-6 and to modified forms of GSP-6 by measuring binding to sulfated (GSP-1) and non-sulfated (GP-1) forms of the N-terminal peptide fragment of PSGL-1 and was compared against two mouse monoclonal antibodies to PSGL-1, KPL1 and PL1. The binding of SelK1 and the mouse monoclonal antibodies was measured in BIACORE analysis. SelK1 bound to GSP-6 and GSP-1, but did not bind GP-1, indicating that the antibody requires sulfation of the N-terminal peptide for binding activity. The KPL1 antibody bound GSP-6, GSP-1 and GP-1 indicating it does not require sulfation of the peptide for binding. The binding of PL1 and hPL1 (a humanized form of PL1) was more complex in that it does not appear to require sulfate, but may require a larger oligosaccharide than the single α-GalNAc on GP-1 and GSP-1 which it bound weakly (FIG. 4).

Figure 5:
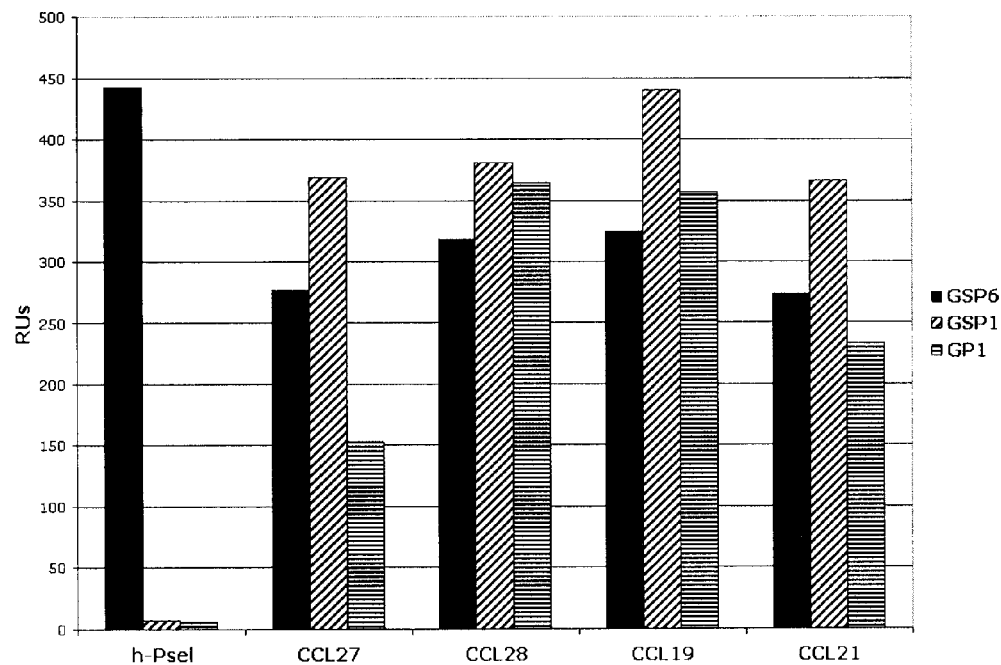
FIG. 5 shows a graph of Surface Plasmon Resonance binding analysis of several chemokines to PSGL-1 glycomimetics. Glycosulfopeptides GSP-6 and GSP-1, and glycopeptide GP-1 were covalently attached to a BIACORE chip and various chemokines were introduced and binding response units were measured. All chemokines tested (CCL27, CCL28, CCL19 and CCL21) bound to PSGL-1 indicating that PSGL-1 functions to bind chemokines that mediate chemotaxis of leukocytes.

Regarding chemokine binding, without wishing to be bound by theory, as discussed above, it is believed that chemokine binding to PSGL-1 plays a major role in lymphocyte homing that precipitates the inflammatory response in Crohn's Disease and other inflammatory diseases. To investigate this, SelK1 antibody was tested for its ability to block chemokine binding to the previously-mentioned peptide fragments of PSGL-1 using a BIACORE assay. To enable this method, we first demonstrated that several chemokines (CCL27, CCL28, CCL19 and CCL21) bind to the PSGL-1 peptide glycomimetics GSP-6, GSP-1 and GP-1 (FIG. 5) which had been coupled to a BIACORE chip. GSP-6, GSP-1 and GP-1 bound to all the chemokines tested, though GP1 bound with less affinity to CCL27 than the other chemokines tested.

Figure 6:
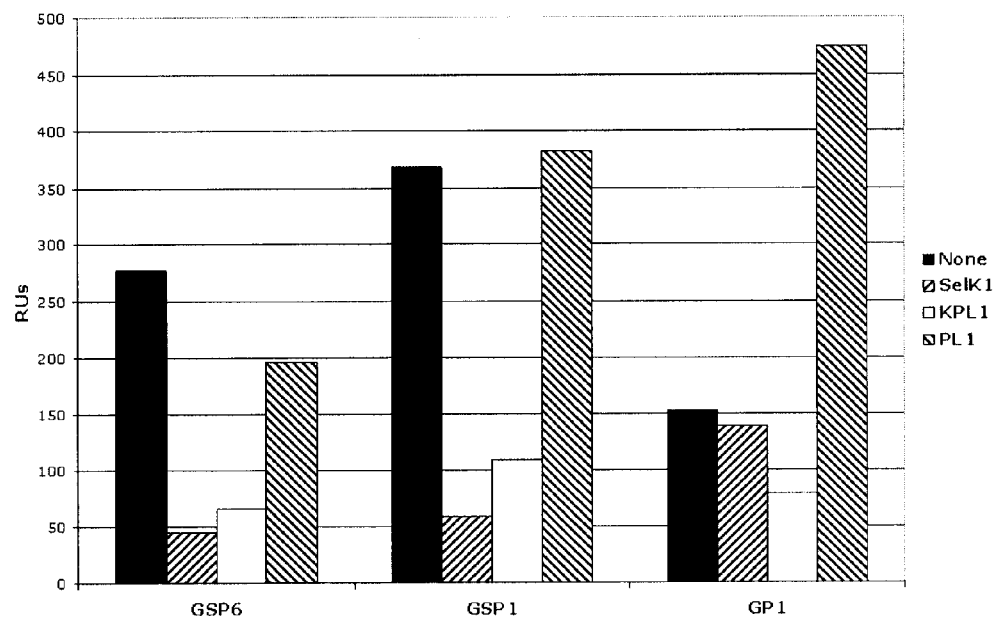
FIG. 6 is a graph showing inhibition of binding of chemokine CCL27 to PSGL-1 peptide glycomimetics by anti-PSGL-1 antibodies. To measure inhibition of chemokine CCL27 binding to PSGL-1, glycosulfopeptides GSP-6 and GSP-1 and glycopeptide GP1 were covalently bound to a BIACORE chip and CCL27 was added in the presence or absence of anti-PSGL-1 antibodies (SelK1 anti-human PSGL-1 antibody, KPL1, and PL1) and response units measured. SelK1 was the most effective anti-PSGL-1 antibody in blocking CCL27 binding to PSGL-1 peptide glycomimetics.
Figure 7:
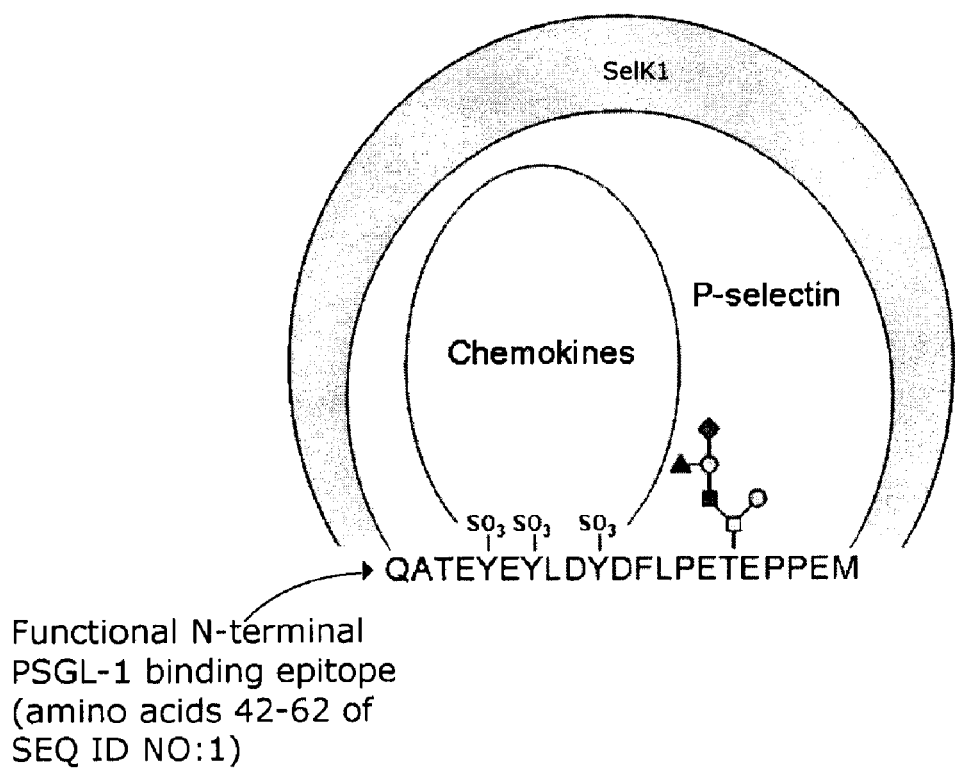
FIG. 7 is a schematic diagram showing the dual function of the SelK1 anti-PSGL-1 antibody in inhibiting adhesion and chemotaxis of inflammatory cell types to leukocyte cells bearing PSGL-1.

The ability of anti-PSGL- antibodies including SelK1 antibody to block CCL27 binding to GSP-6, GSP-1 and GP-1 was tested. Biotinylated peptides were coupled to a streptavidin coated BIACORE chip and chemokines added and binding measured. Anti-PSGL-1 antibodies were added and the effect on chemokine binding assessed. The results demonstrated that SelK1 antibody blocked binding of chemokines (e.g., CCL27) to GSP-6 and GSP-1 (FIG. 6). This novel result demonstrates the dual function of this antibody by both inhibiting chemokine binding to PSGL-1 and blocking P-selectin binding to PSGL-1. SelK1 antibody had no effect on CCL27/GP1 binding consistent with the observation that the SelK1 antibody does not bind the non-sulfated mimetics GP-1 of the N-terminal peptide of PSGL-1. It was verified that KPL-1 does bind GP-1 and as a result this mouse monoclonal antibody did block CCL27 to GP-1 in addition to GSP-6 and GSP-1. PL1 had no effect on the binding of the chemokines tested. These results demonstrate that the SelK1 antibody has dual function properties in blocking P-selectin (and L-selectin) and binding chemokine binding to PSGL-1 (as illustrated in FIG. 7) and thus can be used as a novel therapeutic treatment of Crohn's Disease and other inflammatory diseases as contemplated elsewhere herein.

The present invention is thus directed to antibodies and antigen binding fragments thereof that selectively bind to an N-terminal epitope of PSGL-1 (located within amino acids 42-62 of SEQ ID NO:1) with high specificity and affinity and which have a dual function in substantially blocking the binding both of selectins (particularly P-selectin and L-selectin) and chemokines (e.g., chemokines CCL19, CCL21, CCL27 and CCL28) to PSGL-1 and therefore which represent novel therapeutics for treating inflammatory and thrombotic disorders. Where used herein, the term "substantially blocking" means that the selectins and chemokines bind to PSGL-1 at least 75% below the level observed in controls when the epitope binding antibodies or fragments are not used. The invention is further directed to treatment methods using these dual function antibodies and to pharmaceutical and therapeutic compositions comprising these antibodies for these uses.

The complete amino acid sequence for the SelK1 antibody (and signal peptide sequences), and a DNA sequence which encodes the amino acid sequence of SelK1 is shown in FIG. 8 (A, B) and FIG. 9. In FIGS. 8A and 8B are shown the amino acid sequence and nucleic acid sequence (SEQ ID NO:2 and SEQ ID NO:3, respectively) for the variable component of the heavy chain (VH), the hinge portion, and the three constant units of the heavy chain (CH1, CH2, and CH3) of SelK1. In FIG. 9 are shown the amino acid sequence and nucleic acid sequence (SEQ ID NO:4 and SEQ ID NO:5, respectively) for the variable component of the light chain (VL) and the constant unit of the light chain (CL) of SelK1.

The invention is directed in preferred embodiments to antibodies having sequences substantially as set out herein. As mentioned above, each antibody has three CDRs (complementarity determining regions) in each of the heavy and light variable claims. For example, in the preferred embodiment of the invention comprising the SelK1 antibody, the CDRH1 comprises SEQ ID NO:6, the CDRH2 comprises SEQ ID NO:7, the CDRH3 comprises SEQ ID NO:8, the CDRL1 comprises SEQ ID NO:9, the CDRL2 comprises SEQ ID NO:10, and the CDRL3 comprises SEQ ID NO:11.

The phrase "substantially as set out" means that a particular CDR, in the VL or VH domain will be either identical or highly similar to the specified regions of the sequence as set out herein. For example, such substitutions may include 1 or 2 substitutions, additions, or deletions for every approximately 5 amino acids in the sequence of a CDR (H1, H2, H3, L1, L2, or L3). A sequence is "substantially identical" if it has no more than 1 nucleic acid codon or amino acid residue substituted, deleted, or added for every 10-20 residues in the sequence.

The present invention further comprises antibodies which comprise 1, 2, 3, 4, 5, 6, 7, or 8 to 10 amino acid substitutions in the 6 CDRs as compared to the 6 CDRs of the SelK1 antibody. The substitutions are preferably conservative substitutions but may be any of the other 20 naturally-occurring amino acids which still results in an antibody which binds with a $K_d \leq 100$ nM to PSGL-1. The invention further comprises nucleic acids which encode such antibody variants of SelK1 and vectors and hosts comprising such nucleic acids.

SEQ ID NO:12 shows a DNA sequence which encodes the complete heavy chain sequence (SEQ ID NO:3) with the flanking vector sequence therefor. SEQ ID NO:13 shows a DNA sequence which encodes the complete light chain nucleic acid encoding sequence (SEQ ID NO:5) with the flanking vector sequence therefor.

The present invention in one embodiment contemplates antibodies that specifically bind to human PSGL-1. CDRs in such antibodies are not limited to the specific sequences of VH and VL shown herein and may include variants of these sequences that retain the ability to block P-selectin and chemokine binding to PSGL-1. Such variants may be produced by a skilled artisan using techniques well known in the art. For example, amino acid substitutions, deletions, or additions, can be made in the FRs and/or in the CDRs as described elsewhere herein. While changes in the FRs are usually designed to improve stability and immunogenicity of the antibody, changes in the CDRs are typically designed to increase affinity of the antibody for its target. Variants of FRs also include naturally occurring immunoglobulin allotypes. Such affinity-increasing changes may be determined empirically by routine techniques that involve altering the CDR and testing the affinity antibody for its target.

For example, conservative amino acid substitutions can be made within any one of the disclosed CDRs. Various alterations can be made according to the methods described in *Antibody Engineering*, 2$^{nd}$ ed., Borrebaeck, Ed., Oxford University Press (1995). These include but are not limited to nucleotide sequences that are altered by the substitution of different codons that encode an identical or a functionally equivalent amino acid residue ("conservative substitutions") within the sequence, thus producing a "silent" change. For example, the nonpolar amino acids which may be conservatively substituted include alanine, leucine, isoleucine, valine, proline, phenylalanine, tryptophan, and methionine. The polar neutral amino acids which may be substituted conservatively include glycine, serine, threonine, cysteine, tyrosine, asparagine, and glutamine. The positively charged (basic) amino acids which may be conservatively substituted include arginine, lysine, and histidine. The negatively charged (acidic) amino acids which may be conservatively substituted include aspartic acid and glutamic acid. Substitutes for an amino acid within the sequence may also be selected from other members of the class to which the amino acid belongs.

Derivatives and analogs of antibodies of the invention can be produced by various techniques well known in the art, including recombinant and synthetic methods (Sambrook et al., *Molecular Cloning: A Laboratory Manual*, 2$^{nd}$ ed., Cold Spring Harbor Laboratory Press (1989), and Bodansky et al., *The Practice of Peptide Synthesis*, 2$^{nd}$ ed., Spring Verlag, Berlin, Germany (1995)).

Antibodies in which CDR sequences differ only insubstantially from those of the variable regions of SelK1 are also encompassed within the scope of this invention. As noted above, typically, an amino acid is substituted by a related amino acid having similar charge, hydrophobic, or stereochemical characteristics. Such substitutions would be within the ordinary skills of an artisan. Further, a skilled artisan would appreciate that changes can be made in FRs without adversely affecting the binding properties of an antibody. Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding As noted above, the antibodies of the present invention also block chemokine binding to PSGL-1. Examples of chemokines contemplated herein as blocked by the antibodies of the present invention include, but are not limited to: CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, XCL1, XCL2, and CX3CL1.

In one aspect of present invention, the dual function anti-PSGL-1 antibodies contemplated herein can be used in the treatment of a number of inflammatory and thrombotic disorders in primates (including humans) which involve leukocyte, lymphocyte or endothelial cell adhesion, including, but not limited to, inflammatory bowel diseases (e.g., Crohn's disease, ulcerative colitis, enteritis), arthritis (e.g., rheumatoid arthritis, osteoarthritis, psoriatic arthritis), graft rejection, graft vs. host disease, asthma, chronic obstructive pulmonary disease, psoriasis, dermatitis, nephritis, lupus erythematosis, scleroderma, rhinitis, anaphylaxis, diabetes, multiple sclerosis, atherosclerosis, thrombosis, allergic reactions, thyroiditis and tumor metastasis. The term "primate" as used herein refers to humans, monkeys, and apes such as chimpanzees, gorillas, and orangutans.

As used herein, the "affinity" of the antibody for PSGL-1 is characterized by its $K_d$, or disassociation constant. A stronger affinity is represented by a lower $K_d$ while a weaker affinity is represented by a higher $K_d$. As such, an antibody of the present invention preferably has an affinity represented by a $K_d \leq 100$ nM, or $\leq 50$ nM, or more preferably by a $K_d \leq 25$ nM, and still more preferably by a $K_d \leq 10$ nM, and even more preferably by a $K_d \leq 5$ nM.

An antibody or antibody fragment "homolog," as used herein, means that a relevant amino acid sequence of a protein or a peptide is at least 70%, 75%, 80%, 85%, 90%, 95%, 96%, 97%, 98%, 99%, 99.5%, or 100% identical to a given sequence. By way of example, such sequences may be variants derived from various species, or the homologous sequence may be recombinantly produced. The sequence may be derived from the given sequence by truncation, deletion, amino acid substitution, or addition. Percent identity between two amino acid sequences is determined by standard alignment algorithms such as, for example, Basic Local Alignment Tool (BLAST) described in Altschul et al., J. Mol. Biol. 215:403-410 (1990). Needleman et al., *J. Mol. Biol.* 48:444-453 (1970); Meyers et al., *Comput. Appl. Biosci.* 4:11-17 (1988); or Tatusova et al., *FEMS Microbiol. Left.* 174:247-250 (1999), and other alignment algorithms and methods of the art.

The term "isolated" or "purified" refers to a molecule that is substantially free of its natural environment. For instance, an isolated protein is substantially free of cellular material or other proteins from the cell or tissue source from which it was derived. The term also refers to preparations where the isolated protein is at least 70-80% (w/w) pure; or at least 80-90% (w/w) pure; or at least 90-95% pure; or at least 80%, 85%, 90%, 95%, 96%, 97%, 98%, 99%, or 100% (w/w) pure. In some embodiments, the isolated molecule is sufficiently pure for pharmaceutical compositions.

Inhibitory activity refers to a reduction in an activity of PSGL-1 by a PSGL-1 inhibitor, relative to the activity of PSGL-1 in the absence of the same inhibitor. A neutralizing antibody may reduce one or more PSGL-1 activities. For example, the reduction in activity (e.g., leukocyte adhesion and chemotaxis) is preferably at least about 10%, 20%, 30%, 40%, 50%, 60%, 70%, 75%, 80%, 85%, 90%, 95%, or higher.

The term "PSGL-1 inhibitor" as used herein includes any agent, such as, e.g., a neutralizing antibody, capable of inhibiting activity, expression, processing, or cell surface localization of PSGL-1. Such inhibitors are said to "inhibit," "neutralize," or "reduce" the biological activity of PSGL-1.

The preparation of monoclonal antibodies is conventional and well known to persons of ordinary skill in the art. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, (Nature 256, 495: 1975), or may be made by recombinant methods, e.g., as described in U.S. Pat. No. 4,816,567, for example.

Another method involves humanizing a monoclonal antibody by recombinant means to generate antibodies containing, for example, human or primate specific and recognizable sequences.

Methods of making antibodies of the invention bind with high affinity to human PSGL-1 or to an epitope thereof may comprise transfecting a cell with a DNA construct, the construct comprising a DNA sequence encoding at least a portion of the neutralizing PSGL-1 specific antibodies of the invention, culturing the cell under conditions such that the antibody protein is expressed by the cell, and isolating the antibody protein.

Preferably, the constant region has been modified to modulate (i.e. reduce or enhance) effector function as noted elsewhere as compared to the effector function of a wild-type immunoglobulin heavy chain Fc region. In various embodiments, the IgG constant region has reduced effector function, or alternatively it has increased effector function, for example. Fc effector function includes, for example, antibody-dependent cellular cytotoxicity (ADCC), phagocytosis, complement-dependent cytotoxicity, and half-life or clearance rate function. The IgG amino acid sequence of the Fc domain can be altered to affect binding to Fc gamma receptors (and thus ADCC or phagocytosis functions), or to alter interaction with the complement system (complement-dependent cytotoxicity function).

In one embodiment, the antibody comprises a constant region or Fc portion that has low or no affinity for at least one Fc receptor. In an alternative embodiment, the second polypeptide has low or no affinity for complement protein C1Q. In general, an effector function of an antibody can be altered by altering the affinity of the antibody for an effector molecule such as an Fc receptor. Binding affinity will generally be varied by modifying the effector molecule binding site. Disclosure of IgG modifications that alter interaction with effector molecules such as Fc receptors can be found for example in U.S. Pat. Nos. 5,624,821 and 5,648,260

Antibody proteins of the invention can be produced using techniques well known in the art. For example, the antibody proteins of the invention can be produced recombinantly in cells (see, e.g., Sambrook et al., *Molecular Cloning: A Laboratory Manual*, Cold Spring Harbor Laboratory, N.Y., 1989, and Ausubel et al., *Current Protocols in Molecular Biology*, Greene Publishing Associates and Wiley Interscience, N.Y., 1989).

For recombinant production, a polynucleotide sequence encoding the antibody protein is inserted into an appropriate expression vehicle, such as a vector which contains the necessary elements for the transcription and translation of the inserted coding sequence. The expression vehicle is then transfected into a suitable target cell which will express the peptide. Transfection techniques known in the art include, but are not limited to, calcium phosphate precipitation (Wigler et al., *Cell* 14:725 (1978)) and electroporation (Neumann et al., *EMBO J.* 1:841 (1982)). A variety of host-expression vector systems may be utilized to express the antibody proteins described herein preferably including eukaryotic cells.

The present disclosure further provides isolated nucleic acids encoding the disclosed antibodies. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

In another embodiment, the nucleic acid molecules of the invention also comprise nucleotide sequences that are at least 80% identical to the sequences disclosed herein. Also contemplated are embodiments in which a sequence is at least 85%, 90%, 95%, 96%, 97%, 98%, 99%, or 99.5% identical to a sequence disclosed herein and/or which hybridize to a sequence of the present invention under conditions of high or moderate stringency. The percent identity may be determined by visual inspection and mathematical calculation.

Stringency, including "high stringency," as used herein, includes conditions readily determined by the skilled artisan based on, for example, the length of the DNA. Generally, such conditions are defined as hybridization conditions of 50% formamide, 6×SSC at 42° C. (or other similar hybridization solution, such as, e.g., Stark's solution, in 50% formamide at 42° C.), and with washing at approximately 68° C., 0.2×SSC, 0.1% SDS. The skilled artisan will recognize that the temperature and wash solution salt concentration can be adjusted as necessary according to factors such as the length of the probe.

"Moderate stringency," as used herein, includes conditions that can be readily determined by those having ordinary skill in the art based on, for example, the length of the DNA. The basic conditions are set forth by Sambrook et al., *Molecular Cloning: A Laboratory Manual,* 2d ed., 1:1.101-104, Cold Spring Harbor Laboratory Press (1989), and include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single epitopic site. Furthermore, in contrast to conventional polyclonal antibody preparations that typically include different antibodies directed against different determinants (epitopes), each monoclonal antibody is directed against a single determinant. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567).

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in *E. coli* of DNA encoding the fragment. Antibody fragments, as noted above, can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein, which are hereby expressly incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of VH and VL chains. This association may be non-covalent or the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Another form of an antibody fragment is a peptide coding for a single CDR. CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells.

The invention contemplates engineered antibodies including fully human and humanized forms of non-human (e.g., primate or murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain minimal sequences derived from non-human immunoglobulin. For the most part, humanized antibodies are human immunoglobulins in which residues from a CDR of the recipient are replaced by residues from a CDR of a nonhuman species such as mouse, rat or rabbit having the desired specificity, affinity and capacity.

In making an engineered antibody, a DNA sequence encoding an antibody molecule of the invention is prepared synthetically by established standard methods. For example, according to the phosphoamidine method, oligonucleotides are synthesized, e.g. in an automatic DNA synthesizer, purified, annealed, ligated and cloned in suitable vectors.

The DNA sequence may then be inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

In the vector, the DNA sequence encoding the protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter, the MT-1 (metallothionein gene) promoter or the adenovirus 2 major late promoter. A suitable promoter for use in insect cells is the polyhedrin promoter. Suitable promoters for use in yeast host cells include promoters from yeast glycolytic genes or alcohol dehydrogenase genes or the TPI1 or ADH2-4c promoters. Suitable promoters for use in filamentous fungus host cells are, for instance, the ADH3 promoter or the tpiA promoter.

The DNA coding sequence may also be operably connected to a suitable terminator, such as the human growth hormone terminator or (for fungal hosts) the TPI1 or ADH3 promoters. The vector may further comprise elements such as polyadenylation signals (e.g. from SV 40 or title adenovirus 5 Elb region), transcriptional enhancer sequences (e.g. the SV 40 enhancer) and translational enhancer sequences (e.g., ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the proteins, the promoter and the terminator, respectively, and to insert them into suitable vectors containing the information necessary for replication, are well known to persons skilled in the art.

To obtain recombinant proteins of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or Acharombacter lyticus, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines include, but are not limited to, the HEk293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are well known in the art.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes.

The proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

The antibodies of the present invention preferably include one or more modifications which inactivate complement. The term "complement activity" broadly encompasses the biochemical and physiological activities associated with activation of the complement system, individual complement pathway associated molecules, as well as genes encoding these molecules. Therefore, complement activities include, e.g., structure and expression of a gene encoding a complement pathway molecule, biochemical activity (e.g., enzymatic or regulatory) of a complement pathway molecule, cellular activities that initiate or result from activation of the complement system, and presence of serum autoantibodies against complement pathway molecules. In SelK1 the preferred modification to inactivate complement is a replacement of Lys with Ala at position 341 (of SEQ ID NO:2) in the heavy chain constant region CH2. Other substitutions for Lys at the same position may include for example any of gly, leu, trp, tyr, pro, thr, ser, met, asp, asn, glu, gln, phe, ile, val, thr, and cys and which are effective in inactivating complement.

The terms "complement pathway associated molecules," "complement pathway molecules," and "complement pathway associated proteins" are used interchangeably and refer to the various molecules that play a role in complement activation and the downstream cellular activities mediated by, responsive to, or triggered by the activated complement system. They include initiators of complement pathways (i.e., molecules that directly or indirectly triggers the activation of complement system), molecules that are produced or play a role during complement activation (e.g., complement proteins/enzymes such as C3, C5, C5b-9, Factor B, MASP-1, and MASP-2), complement receptors or inhibitors (e.g., clusterin, vitronectin, CR1, or CD59), and molecules regulated or triggered by the activated complement system (e.g., membrane attack complex-inhibitory factor, MACIF. Thus, in addition to complement proteins noted above, complement pathway associated molecules also include, e.g., C3/C5 convertase regulators (RCA) such as complement receptor type 1 (also termed CR1 or CD35), complement receptor type 2 (also termed CR2 or CD21), membrane cofactor protein (MCP or CD46), and C4bBP; MAC regulators such as vitronectin, clusterin (also termed "SP40,40"), CRP, CD59, and homologous restriction factor (HRF); immunoglobulin chains such as Ig kappa, Ig lambda, or Ig gamma; C1 inhibitor; and other proteins such as CR3, CR4 (CD11b/18), and DAF (CD 55).

Antibodies of the present invention provided by any of the above described methods are preferably used in the manufacture of a medicament or composition for the treatment of a pathological condition, wherein inhibiting a inflammatory response is required such as is contemplated herein.

It is an important objective of the present invention to use the antibodies, functionally active fragments or variants of said antibodies for the manufacture of a medicament or composition for prevention and/or treatment of inflammatory responses or diseases such as described herein.

In one embodiment the invention relates to the manufacture of a therapeutic medicament or composition which is capable of being used for prevention and/or treatment of an inflammatory bowel disease such as Crohn's disease or ulcerative colitis. Other examples of inflammatory responses, which may be harmful for an individual and therefore are advantageously being suppressed include but are not limited by conditions associated with extensive trauma, or chronic inflammation, such as for example type IV delayed hypersensitivity, associated for example with infection by Tubercle bacilli, or systematic inflammatory response syndrome, or multiple organ failure, or rheumatoid arthritis or other conditions described herein.

The SAMP-1/Yit mouse model of spontaneous iletis closely resembles human Crohn's Disease. Therapeutic inhibition of PSGL-1 uniquely ameliorates ileitis in this model whereas blockade of individual selectins does not. Inhibition of TNF in this model does reduce the severity of ileitis in a manner similar to anti-PSGL-1 although the therapeutic effect does not appear to be as potent as anti-GSGL-1 [127]. Thus, the SAMP-1 model appears to closely mirror human Crohn's Disease not only in its pathophysiology but also in its response to therapeutic intervention. This evidence supports the conclusion that therapeutic substances which inhibit PSGL-1 binding activity in humans (and other primates) would also be effective as treatments of Crohn's diseases, as well as other inflammatory diseases as discussed elsewhere herein.

In the pharmaceutical composition of a medicament according to the present invention, the antibodies may be formulated by any of the established methods of formulating pharmaceutical compositions, e.g. as described in the latest edition of Remington's Pharmaceutical Sciences. The composition may typically be in a form suited for local or systemic injection or infusion and may, as such, be formulated with sterile water or an isotonic saline or glucose solution. The compositions may be sterilized by conventional sterilization techniques, which are well known in the art. The resulting aqueous solutions may be packaged for use or filtered under aseptic conditions and lyophilised, the lyophilised preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc. The concentration of proteins may vary widely, for example, from less than about 0.01% to as much as 15-20% or more by weight. A unit dosage of the composition may contain for example from about 1 μg to about 1000 mg of an antibody or antibody fragment.

The antibodies or antibody fragments may be administered topically or by injection. Dosages will be prescribed by the physician according to the particular condition and the particular individual to be treated. Dosages and frequency is carefully adapted and adjusted according to parameters determined by the physician in charge. Preferred administration routes may be subcutaneous, intravenous, intramuscular, intratracheal, intravesical, intratracheal or intraperitoneal injections and may be given per 24 to 48 hours, or per week, every 14 days, every 4 weeks for example in the range of from 0.1-1000 mg, especially 1 mg to 100 mg, in particular 1-10 mg per kg body weight. The dose may be administered continuously through a catheter or in individual boluses. The antibody of the invention may be administered in an efficacious quantity between 1 μg/kg to 10 μg/kg, 10 μg/kg to 100 μg/kg, 100 μg/kg to 1 mg/kg, 1 mg/kg to 10 mg/kg, and 10 mg/kg to 50 mg/kg or 10 mg/kg to 100 mg/kg body weight.

Compositions of a medicament used in the present invention comprising antibodies described herein may additionally be supplemented by other therapeutic compounds which are routinely prescribed by the physician according to the particular condition and the particular individual to be treated such as an anti-inflammatory drug, wherein said drugs are prescribed by the physician according to the particular condition and the particular individual to be treated.

PSGL-1 has functional importance in leukocyte platelet, and/or microvesicle adhesion, rolling, recruitment, aggregation; leukocyte secretion of cytokines; promotion of coagulation; and other aspects of inflammation, thrombosis, coagulation, immune response, and signal transduction. PSGL-1 is also involved in tumor metastasis. A neutralizing antibody described herein will inhibit one or more of these PSGL-1 activities, in vivo or in vitro, for example. Thus, the inhibition of PSGL-1 with a neutralizing antibody described herein is useful in the treatment of various disorders associated with inflammation, thrombosis, coagulation, T cell response, as well as in the treatment of immune and cardiovascular disorders, for example.

As noted above, in one embodiment of the invention, the antibodies of fragments thereof of the present invention are used in the treatment of inflammatory bowel diseases, including Crohn's disease and ulcerative colitis. Inflammatory Bowel Disease ("IBD") is the collective term used to describe two chronic, idiopathic inflammatory diseases of the gastrointestinal tract: ulcerative colitis ("UC") and Crohn's disease ("CD"). UC and CD are considered together because of their overlapping clinical, etiologic, and pathogenetic features. From a therapeutic and prognostic standpoint, however, it is useful to distinguish them.

IBD occurs world-wide and is reported to afflict as many as two million people. Onset has been documented at all ages; however, IBD predominately begins in young adulthood. The three most common presenting symptoms of IBD are diarrhea, abdominal pain, and fever. The diarrhea may range from mild to severe and is often accompanied by urgency and frequency. In UC, the diarrhea is usually bloody and may contain mucus and purulent matter as well. Anemia and weight loss are additional common signs of IBD. Reports of an increasing occurrence of psychological problems, including anxiety and depression, are perhaps not surprising secondary effects of what is often a debilitating disease that occurs in people in the prime of life.

A battery of laboratory, radiological, and endoscopic evaluations are combined to derive a diagnosis of IBD and to assess the extent and severity of the disease. Nevertheless, differentiating UC from CD, as well as other types of inflammatory conditions of the intestines, such as irritable bowel syndrome, infectious diarrhea, rectal bleeding, radiation colitis, and the like, is difficult, because the mucosa of the small and large intestines reacts in a similar way to a large number of different insults. Once other types of bowel disorders have been ruled out, the final diagnosis is often made on the basis of the progression of the disease. In many patients, though, the colitis must still be regarded as indeterminate because of the overlapping features of UC and CD, particularly with CD of the colon.

The leading early symptoms of UC and CD are chronic recurrent diarrhea, bloody diarrhea, recurrent abdominal pain, nausea, weight loss general evidence of inflammation without any obvious explanation (fever, raised ESR, leucocytosis, thrombocytosis and dysproteinenemia or anemia). Among these symptoms, diarrhea and anemia are more characteristic of UC while pain and weight loss and marked evidence of inflammation are more common in CD. While the history and physical examination of a patient can help, the final confirmation of the diagnosis has traditionally been made endoscopically, histologically and, in relation to the small intestine, radiologically as well.

The PSGL-1 specific antibodies described herein can be linked to another molecule. For example, antibodies may be linked to another peptide or protein, toxin, radioisotope, cytotoxic or cytostatic agents. The antibodies can be linked covalently by chemical cross-linking or by recombinant methods. The antibodies may also be linked to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their stability or half-life. Exemplary polymers and methods to attach them are also shown in U.S. Pat. Nos. 4,766,106; 4,179,337; 4,495,285; and 4,609,546.

The antibodies may also be tagged with a detectable label. A detectable label is a molecule which, by its chemical nature, provides an analytically identifiable signal which allows the detection of a molecular interaction. A protein, including an antibody, has a detectable label if it is covalently or non-covalently bound to a molecule that can be detected directly (e.g., by means of a chromophore, fluorophore, or radioisotope) or indirectly (e.g., by means of catalyzing a reaction producing a colored, luminescent, or fluorescent product). Detectable labels include a radiolabel such as $^{131}$I or $^{99}$Tc, a heavy metal, or a fluorescent substrate, such as Europium, for example, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

The present invention is also directed to methods of screening for substances such as, but not limited to, anti-PSGL-1 antibodies and binding fragments thereof which block both selectin binding and chemokine binding to PSGL-1, particularly to a portion of the epitope of amino acids 42-62 thereof.

As noted above, the present invention is directed to antibodies against PSGL-1, host cells that produce such anti-PSGL-1 antibodies, vectors that contain DNA which encode such anti-PSGL-1 antibody production and methods to identify dual function anti-PSGL-1 antibodies which block both selectin-mediated adhesion of leukocytes and chemokine-mediated chemotaxis of leukocytes.

In one embodiment the invention is directed to methods of identifying antibodies that specifically bind to at least a portion of a polypeptide comprising amino acids 42-62 of human PSGL-1 (SEQ ID NO:1) and which block at least one of P- or L-selectin from binding thereto, and block at least one chemokine (including, but not limited to, CCL19, CCL21, CCL27, and CCL28) from binding thereto, thus exhibiting a dual function in blocking selectin-mediated adhesion and chemokine-mediated chemotaxis of leukocytes.

The screening method in a preferred embodiment comprises in vitro assays that can be used to measure binding of selectins and chemokines to PSGL-1 and to identify blocking anti-PSGL-1 antibodies that abolish leukocyte or lymphocyte adherence and chemotaxis mediated by chemokine binding to PSGL-1. Test anti-PSGL-1 antibodies can be screened for dual function capability with a series of assays such as, but not limited to, those described herein which will identify those antibodies that bind to PSGL-1 and block the binding epitope thereon for P- and L-selectin and chemokines which is encompassed by residues 42-62 of the PSGL-1 native protein. Previously identified anti-PSGL-1 antibodies have been shown to block binding of P- and L-selectin, but not E-selectin, to PSGL-1 and binding of neutrophils to activated endothelial cells, but have not been shown to block chemokine binding or chemotaxis. Non-blocking mouse monoclonal antibodies to epitopes outside the 42-62 domain of PSGL-1, for example PL2 which binds to residues 188-258 of the native protein, can be used as controls in such assays.

In one step of the screening method, test antibodies to PSGL-1 that have been shown to block binding of PSGL-1 to selectins and block binding of neutrophils to selectins or activated endothelial cells, are identified. These test antibodies are further screened to determine their ability to block binding of one or more chemokines, for example CCL19, CCL21, CCL27, and CCL28, to PSGL-1 and to block chemotaxis of neutrophils or lymphocytes mediated by such chemokines. Test antibodies identified as having dual function of blocking both selectin and chemokine targets and function comprise the antibodies of the present invention or those used in the methods of the present invention.

In one embodiment of the method, antibodies which block binding of PSGL-1 to P- and L-selectins are first identified. For example, an ELISA is performed using synthetic, recombinant or soluble forms of P-, E- or L-selectin, or portions of each encompassing the lectin domain, may be immobilized at increasing site densities in microtiter wells. Recombinant or soluble PSGL-1, or fusion proteins or fragments thereof containing residues 42-62 of PSGL-1, may be labeled with a suitable reporter, for example FITC, and added to such wells, incubated, washed and the binding of PSGL-1 to the selectin measured. A test antibody is added to the assay prior to addition of PSGL-1 (or combined with PSGL-1 prior to its addition to the wells) and the signal from wells that contain known non-blocking control antibodies, no antibody, or microtiter wells coated with a non-selectin protein is compared to the signal measured from wells having the PSGL-1 test antibody mixture. A test antibody should preferably effectively block 75-100% of PSGL-1 binding to be advanced to the next step.

In yet another embodiment, human neutrophils or promyelocytic HL-60 cells, which express PSGL-1 on their cell surfaces, can be incubated in such wells and their adhesion to P-, E- or L-selectin measured, for example using the method described below. Human neutrophils may be isolated from heparinized whole blood by density gradient centrifugation. Human HL-60 cells derived from peripheral blood leukocytes expressing human PSGL-1 may be obtained from the ATCC (e.g., ATCC CCL 240). Such cells may be added to the microtiter wells and incubated in the presence or absence of the candidate antibody for a sufficient time (e.g. 30 min.), washed and then quantitated with a myeloperoxidase assay. Myeloperoxidase is measured using the tetramethylbenszidine (TMB) technique (e.g., see Suzuki et al., Anal Biochem 1983). Neutrophils are solubilized by addition of 0.5% hexadecyltrimethylammonium bromide in 0.05 mol/L potassium phosphate buffer, pH 6.0. Samples of the extract are then added to microtiter wells containing 0.08 mol/L potassium phosphate buffer, pH 5.4, 0.5 mol/L hydrogen peroxide, and 0.16 mmol/L TMB. The samples are incubated at 37° C. with shaking for 20 min. The absorbance is measured at 650 nm. The number of cells bound is derived from a standard curve of myeloperoxidase activity versus numbers of cells. An antibody which significantly blocks neutrophil adhesion to P- or L-selectin when compared to a non-blocking antibody to PSGL-1 is advanced to the next testing step. In another embodiment, Chinese hamster ovary (CHO) or COS-7 cells may be transfected with P-, L- or E-selectin DNA so as to express such selectins on their cell surfaces. Such cells are plated as monolayers on microtiter plates in a suitable media to which neutrophils or HL-60 cells can be added. Neutrophils or HL-60 cells may be preincubated with candidate antibodies and added to the microtiter wells. A test antibody which significantly blocks adhesion of neutrophils or HL-60 cells as measured by the myeloperoxidase assay when compared to non-blocking antibody controls will be advanced to the next step.

In yet another embodiment of the invention, test antibodies can be screened for their ability to bind PSGL-1 and block P-selectin function under flow conditions that simulate physiological blood flow, for example in a method shown below. Physiological flow conditions are produced in vitro using a flow chamber with parallel-plate geometry (e.g., Lawrence et al; 1987 Blood). Human umbilical vein endothelial cells are cultured in dishes which can be place into the flow chamber. Isolated neutrophils are diluted in a buffered saline solution with calcium and magnesium and perfused through the chamber at a rate that produces the desired wall shear stress. Stimuli such as histamine or thrombin may be added directly to this feed solution so that endothelial cells are stimulated for the duration of the experiment. Interactions between neutrophils and the endothelial monolayer are observed by phase-contrast video microscopy and quantified with a digital image processing system. Rolling and firmly adherent neutrophils are counted using methods that are know to those skilled in the art for each of three fields and averaged to give the values at that time point. To screen for anti-PSGL-1 antibodies that block adherence under flow, anti-PSGL-1 mAbs, and non-blocking control anti-PSGL-1 antibodies, may be added to the neutrophil suspension and perfused over the endothelial cell layer at various concentrations. Test antibodies to PSGL-1 that significantly block neutrophil adhesion under flow are advanced to the next step of the screening method.

Test antibodies which are identified as effective in blocking a selectin from binding to the PSGL-1 epitope encompassed by a portion of residues 42-62, will be further screened for their ability to block binding of chemokines or chemotaxis to PSGL-1. Chemokines used in the assays, in particular CCL19, CCL21 CCL27, and CCL28, may be obtained commercially, or chemically synthesized with tBoc (tertiary butyloxycarbonyl) solid-phase chemistry, purified by high-performance liquid chromatography and their mass confirmed by electrospray mass spectrometry. Synthetic chemokines prepared in this way can be used for assays. Chemokines may also be biotinylated by coupling of biotinamidohexanoic acid N-hydroxysuccinimide ester to the N-terminus of the chemokine before deprotection and refolding of the chemokine. The biotinylated-chemokine can be labeled by addition of streptavidin conjugated to fluorescence reporters, for example FITC, or other flurophores suitable for fluorescence detection. For example, biotinylated-chemokines can be mixed in a suitable buffer with fluoroscein isothiocyante (FITC)-streptavidin and preincubated for 30 min. prior to a chemotaxis assay.

In one embodiment, test antibodies can be screened for the ability to block chemokine binding to PSGL-1 by using a dot-blot assay. In such assays the chemokines, for example CCL19, CCL21, CCL27, and/or CCL28, are dot-blotted onto nitrocellulose membranes in replicate dots at 25-400 ng per dot. Recombinant human PSGL-Ig may be obtained commercially or can be prepared from a cell expression system transfected with a vector encoding a recombinant form of PSGL-1 and human IgG [20]. Such vector may contain native PSGL-1 or fragments thereof fused to human IgG, but must at least contain the N-terminal domain containing the functional epitope for selectins and chemokines encompassed by residues 42-62 of the SEQ ID NO:1. The membranes are blocked for 2 hours with 5% BSA in Tris-buffered saline and then incubated for 2 hours with 50 ug/ml of PSGL-1-IgG in the presence or absence of the test antibody, or with a non-function-blocking control anti-PSGL-1 antibody, for example PL2. The membranes are washed and binding is detected by addition of an anti-human IgG labeled with a fluorophore, for example FITC, or chromogenic agent, for example horseradish peroxidase, for detection and analysis. A test antibody which significantly blocks binding of the PSGL-1-IgG to the presented chemokines when compared to control non-blocking antibodies is considered to be a successful dual-function-blocking antibody as contemplated in the present invention.

In another embodiment, an additional step to determine if chemokine blocking antibodies to PSGL-1 can block chemokine mediated chemotaxis, cell binding and chemotaxis assays may be performed with leukocytes or lymphocytes. Human neutrophils are isolated from heparinized blood by dextran sedimentation, hypotonic lysis and Ficoll-Paque density gradient centrifugation [20]. Lymphocytes may be isolated as single-cell suspensions derived from superficial cervical, brachial, inguinal, mesenteric and axillary lymph nodes. Cells may then be dissociated by passing through a stainless steel sieve in a suitable medium, for example RPMI medium (75). Cells may be labeled with cell specific antibodies labeled with a suitable fluorophore, for example neutrophils may be labeled with anti-CD43-FITC, or lymphocytes may be labeled anti-CD4-FITC or anti-CD8-FITC. Cell binding assays may be performed using FACs analysis. In such assays, labeled neutrophils or lymphocytes are mixed with one or more chemokines, including for example CCL19, CCL21, CCL27 and CCL28, which are suitably labeled for FACs analysis, for example with phycoerythrin, and mixed with antibodies to PSGL-1 or non-blocking control antibodies to PSGL-1. A test antibody which significantly blocks binding of the neutrophils or lymphocytes to the presented chemokines when compared to control non-blocking antibodies is considered to be a successful dual-function-blocking antibody as contemplated by the present invention.

In yet another embodiment of an assay to screen an antibody to PSGL-1 for its ability to block chemokine mediated chemotaxis, a chemotaxis buffer containing a chemokine, for example CCL19, CCL21, CCL27 and CCL28, may be added to the lower chamber of a transwell plate. Cells of interest, typically suitably labeled neutrophils or lymphocytes, are resuspended at a density of $10\times10^6$ viable cells per milliliter (100 µl) in chemotaxis buffer prewarmed to 37° C. and added to the upper transwell chamber, followed by incubation for 2-3 hours at 37° C. In an antibody inhibition assay, 50 µl of anti-PSGL-1 antibody, or a control non-blocking antibody to PSGL-1, may be added to the upper transwell chamber first, followed by 50 µl of cells at a density of $20\times10^6$ viable cells per milliliter. Cells that migrate to the lower chamber are quantified by flow cytometry. A test antibody to PSGL-1 which significantly blocks leukocyte or lymphocyte migration when compared to controls is considered to be a successful dual-function-blocking antibody as contemplated by the present invention. Examples of individual components of the methods used herein are shown for example in Moore et al [20, 30], and Veerman et al [75]. Such antibodies identified by the method will have demonstrated a dual function in blocking both selectin and chemokine binding to PSGL-1, and a functional blocking of cell adhesion and homing mediated by PSGL-1 binding to selectins and chemokines, thus identifying antibodies which can be used in accordance with the present invention for therapeutic treatments as contemplated herein or any other use or treatment in which the properties of such antibodies have utility.

In an alternative embodiment of a method of screening test antibodies to identify those that block binding of selectins to the epitope comprising residues 42-62 of PSGL-1, in one embodiment, an ELISA is performed using recombinant PSGL-1, or PSGL-1 purified from human epitope membranes using methods known to those of ordinary skill in the art, or Ig fusion proteins containing the residue 42-62 epitope of PSGL-1, or COS cells transfected with cDNA encoding and expressing PSGL-1. Such forms of PSGL-1 or PSGL-1-containing fragments may be immobilized at increasing site densities in microtiter wells and probed with suitably labeled selectins and chemokines. Selectins may be expressed as recombinant forms of a fusion protein which includes the lectin and EGF domains of P- or L-selectin fused to an immunoglobulin (Ig fusion protein) to produce a bivalent form of the selectin. Such selectins may be labeled with a suitable reporter, for example FITC. The microtiter wells may be incubated in the presence or absence of a candidate (test) anti-PSGL-1 antibody, or a non-blocking (control) antibody. After incubation, the wells may be washed and the binding of PSGL-1 to the selectin measured as relative fluorescence units. Test antibodies are compared to control antibodies and should effectively block 75-100% of PSGL-1 binding to P- and L-selectin. Antibodies which bind to PSGL-1 and block P- or L-selectin binding thereto may be further tested for effectiveness in blocking binding of chemokines to PSGL-1.

An alternate embodiment of the screening method of the present invention contemplates simultaneously screening for antibodies that block binding of selectins and chemokines to PSGL-1 epitope comprising residues 42-62 of SEQ ID NO:1. In one embodiment, an ELISA is performed using recombinant PSGL-1, or PSGL-1 purified from human neutrophil membranes by those skilled in the art, or fusion proteins containing residues 42-62 of PSGL-1. Such PSGL-1 or PSGL-1 epitope may be immobilized at increasing site densities in microtiter wells and probed with suitably labeled selectins and chemokines. Selectins may be expressed as recombinant forms of a fusion protein which includes the lectin and EGF domains of P- or L-selectin fused to an immunoglobulin (Ig fusion protein) to produce a bivalent form of the selectin. Such selectins may be labeled with a suitable reporter, for example FITC. Likewise, chemokines, for example CCL19, CCL21, CCL27 and CCL28, may be synthesized by those skilled in the art and coupled at their N-terminus to biotin. The biotinylated-chemokine may be labeled by addition of streptavidin conjugated to a suitable fluorescent reporter whose emission spectra is shifted from FITC, such as DAPI, or Cy3, or Cy5 or other such dyes. The microtiter wells may be incubated in the presence or absence of a candidate anti-PSGL-1 antibody, or a non-blocking antibody (control). Suitably labeled selectins and chemokines are added simultaneously to the microtiter wells and incubated. After incubation, the wells may be washed and the binding of PSGL-1 to the selectin and chemokine measured as relative fluorescence units (RFU). Test antibodies are compared to control antibodies and those that block 75-100% of PSGL-1 binding to the selectin and chemokine are designated as dual function PSGL-1 blocking antibodies which are contemplated for use in the therapeutic treatments of the present invention as described herein.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention.

The present invention is not to be limited in scope by the specific embodiments or examples of methods and compositions described herein, since such embodiments or examples are intended as but single illustrations of one aspect of the invention and any functionally equivalent embodiments are within the scope of this invention. Indeed, various modifications of the methods and compositions of the invention in addition to those shown and described herein will become apparent to those skilled in the art form the foregoing description.

Each of the references, including U.S. or foreign patents, or published U.S. or foreign applications or publications, cited herein is expressly incorporated herein by reference in its entirety.

REFERENCES CITED

1. Konstantopoulos, K. and L. V. McIntire, *Effects of fluid dynamic forces on vascular cell adhesion.* J Clin Invest, 1997. 100(11 Suppl): p. S19-23.

2. Springer, T. A., *Traffic signals on endothelium for lymphocyte recirculation and leukocyte emigration.* Annu Rev Physiol, 1995. 57: p. 827-72.

3. Zimmerman, G. A., T. M. McIntyre, and S. M. Prescott, *Adhesion and signaling in vascular cell—cell interactions.* J Clin Invest, 1996. 98(8): p. 1699-702.

4. McEver, R. P., K. L. Moore, and R. D. Cummings, *Leukocyte trafficking mediated by selectin-carbohydrate interactions.* J Biol Chem, 1995. 270(19): p. 11025-8.

5. Kansas, G. S., *Selectins and their ligands: current concepts and controversies.* Blood, 1996. 88(9): p. 3259-87.

6. Lowe, J. B. and P. A. Ward, *Therapeutic inhibition of carbohydrate-protein interactions in vivo.* J Clin Invest, 1997. 100(11 Suppl): p. S47-51.

7. Varki, A., *Selectin ligands: will the real ones please stand up?* J Clin Invest, 1997. 100(11 Suppl): p. S31-5.

8. Somers, W. S., et al., *Insights into the molecular basis of leukocyte tethering and rolling revealed by structures of P- and E-selectin bound to SLe(X) and PSGL-1*. Cell, 2000. 103(3): p. 467-79.

9. Smithson, G., et al., *Fuc-TVII is required for T helper 1 and T cytotoxic 1 lymphocyte selectin ligand expression and recruitment in inflammation, and together with Fuc-TIV regulates naive T cell trafficking to lymph nodes*. J Exp Med, 2001. 194(5): p. 601-14.

10. Homeister, J. W., et al., *The alpha(1,3)fucosyltransferases FucT-IV and FucT-VII exert collaborative control over selectin-dependent leukocyte recruitment and lymphocyte homing*. Immunity, 2001. 15(1): p. 115-26.

11. Moore, K. L., et al., *Identification of a specific glycoprotein ligand for P-selectin (CD62) on myeloid cells*. J Cell Biol, 1992. 118(2): p. 445-56.

12. Norgard, K. E., et al., *Characterization of a specific ligand for P-selectin on myeloid cells. A minor glycoprotein with sialylated O-linked oligosaccharides*. J Biol Chem, 1993. 268(17): p. 12764-74.

13. Ushiyama, S., et al., *Structural and functional characterization of monomeric soluble P-selectin and comparison with membrane P-selectin*. J Biol Chem, 1993. 268(20): p. 15229-37.

14. Leppanen, A., et al., *A novel glycosulfopeptide binds to P-selectin and inhibits leukocyte adhesion to P-selectin*. J Biol Chem, 1999. 274(35): p. 24838-48.

15. Leppanen, A., et al., *Binding of glycosulfopeptides to P-selectin requires stereospecific contributions of individual tyrosine sulfate and sugar residues*. J Biol Chem, 2000. 275 (50): p. 39569-78.

16. Sako, D., et al., *Expression cloning of a functional glycoprotein ligand for P-selectin*. Cell, 1993. 75(6): p. 1179-86.

17. Zhou, Q., et al., *The selectin GMP-140 binds to sialylated, fucosylated lactosaminoglycans on both myeloid and nonmyeloid cells*. J Cell Biol, 1991. 115(2): p. 557-64.

18. Yang, J., et al., *Mouse P-selectin glycoprotein ligand-1: molecular cloning, chromosomal localization, and expression of a functional P-selectin receptor*. Blood, 1996. 87(10): p. 4176-86.

19. Veldman, G. M., et al., *Genomic organization and chromosomal localization of the gene encoding human P-selectin glycoprotein ligand*. J Biol Chem, 1995. 270(27): p. 16470-5.

20. Moore, K. L., et al., *P-selectin glycoprotein ligand-1 mediates rolling of human neutrophils on P-selectin*. J Cell Biol, 1995. 128(4): p. 661-71.

21. Wilkins, P. P., et al., *Tyrosine sulfation of P-selectin glycoprotein ligand-1 is required for high affinity binding to P-selectin*. J Biol Chem, 1995. 270(39): p. 22677-80.

22. Pouyani, T. and B. Seed, *PSGL-1 recognition of P-selectin is controlled by a tyrosine sulfation consensus at the PSGL-1 amino terminus*. Cell, 1995. 83(2): p. 333-43.

23. Sako, D., et al., *A sulfated peptide segment at the amino terminus of PSGL-1 is critical for P-selectin binding*. Cell, 1995. 83(2): p. 323-31.

24. Wilkins, P. P., R. P. McEver, and R. D. Cummings, *Structures of the O-glycans on P-selectin glycoprotein ligand-1 from HL-60 cells*. J Biol Chem, 1996. 271(31): p. 18732-42.

25. De Luca, M., et al., *A novel cobra venom metalloproteinase, mocarhagin, cleaves a 10-amino acid peptide from the mature N terminus of P-selectin glycoprotein ligand receptor, PSGL-1, and abolishes P-selectin binding*. J Biol Chem, 1995. 270(45): p. 26734-7.

26. Li, F., et al., *Visualization of P-selectin glycoprotein ligand-1 as a highly extended molecule and mapping of protein epitopes for monoclonal antibodies*. J Biol Chem, 1996. 271(11): p. 6342-8.

27. Walcheck, B., et al., *Neutrophil-neutrophil interactions under hydrodynamic shear stress involve L-selectin and PSGL-1. A mechanism that amplifies initial leukocyte accumulation of P-selectin in vitro*. J Clin Invest, 1996. 98(5): p. 1081-7.

28. Tu, L., et al., *L-selectin binds to P-selectin glycoprotein ligand-1 on leukocytes: interactions between the lectin, epidermal growth factor, and consensus repeat domains of the selectins determine ligand binding specificity*. J Immunol, 1996. 157(9): p. 3995-4004.

29. Spertini, O., et al., *P-selectin glycoprotein ligand 1 is a ligand for L-selectin on neutrophils, monocytes, and CD34+ hematopoietic progenitor cells*. J Cell Biol, 1996. 135(2): p. 523-31.

30. Moore, K. L., et al., *The P-selectin glycoprotein ligand from human neutrophils displays sialylated, fucosylated, O-linked poly-N-acetyllactosamine*. J Biol Chem, 1994. 269 (37): p. 23318-27.

31. Asa, D., et al., *The P-selectin glycoprotein ligand functions as a common human leukocyte ligand for P- and E-selectins*. J Biol Chem, 1995. 270(19): p. 11662-70.

32. Lenter, M., et al., *Monospecific and common glycoprotein ligands for E- and P-selectin on myeloid cells*. J Cell Biol, 1994. 125(2): p. 471-81.

33. Guyer, D. A., et al., *P-selectin glycoprotein ligand-1 (PSGL-1) is a ligand for L-selectin in neutrophil aggregation*. Blood, 1996. 88(7): p. 2415-21.

34. Li, F., et al., *Post-translational modifications of recombinant P-selectin glycoprotein ligand-1 required for binding to P- and E-selectin*. J Biol Chem, 1996. 271(6): p. 3255-64.

35. Goetz, D. J., et al., *Isolated P-selectin glycoprotein ligand-1 dynamic adhesion to P- and E-selectin*. J Cell Biol, 1997. 137(2): p. 509-19.

36. Patel, K. D., M. U. Nollert, and R. P. McEver, *P-selectin must extend a sufficient length from the plasma membrane to mediate rolling of neutrophils*. J Cell Biol, 1995. 131(6 Pt 2): p. 1893-902.

37. Xia, L., et al., *P-selectin glycoprotein ligand-1-deficient mice have impaired leukocyte tethering to E-selectin under flow*. J Clin Invest, 2002. 109(7): p. 939-50.

38. Laszik, Z., et al., *P-selectin glycoprotein ligand-1 is broadly expressed in cells of myeloid, lymphoid, and dendritic lineage and in some nonhematopoietic cells*. Blood, 1996. 88(8): p. 3010-21.

39. Vachino, G., et al., *P-selectin glycoprotein ligand-1 is the major counter-receptor for P-selectin on stimulated T cells and is widely distributed in non-functional form on many lymphocytic cells*. J Biol Chem, 1995. 270(37): p. 21966-74.

40. Moore, K. L. and L. F. Thompson, *P-selectin (CD62) binds to subpopulations of human memory T lymphocytes and natural killer cells*. Biochem Biophys Res Commun, 1992. 186(1): p. 173-81.

41. Diacovo, T. G., et al., *Interactions of human alpha/beta and gamma/delta T lymphocyte subsets in shear flow with E-selectin and P-selectin*. J Exp Med, 1996. 183(3): p. 1193-203.

42. Zanneftino, A. C., et al., *Primitive human hematopoietic progenitors adhere to P-selectin (CD62P)*. Blood, 1995. 85(12): p. 3466-77.

43. Geng, J. G., et al., *Expression of a P-selectin ligand in zona pellucida of porcine oocytes and P-selectin on acroso-* mal membrane of porcine sperm cells. Potential implications for their involvement in sperm-egg interactions. J Cell Biol, 1997. 137(3): p. 743-54.

44. Patel, K. D. and R. P. McEver, *Comparison of tethering and rolling of eosinophils and neutrophils through selectins and P-selectin glycoprotein ligand-1*. J Immunol, 1997. 159(9): p. 4555-65.

45. Weyrich, A. S., et al., *Monocyte tethering by P-selectin regulates monocyte chemotactic protein-1 and tumor necrosis factor-alpha secretion. Signal integration and NF-kappa B translocation*. J Clin Invest, 1995. 95(5): p. 2297-303.

46. Weyrich, A. S., et al., *Activated platelets signal chemokine synthesis by human monocytes*. J Clin Invest, 1996. 97(6): p. 1525-34.

47. Borges, E., et al., *The P-selectin glycoprotein ligand-1 is important for recruitment of neutrophils into inflamed mouse peritoneum*. Blood, 1997. 90(5): p. 1934-42.

48. Bruehl, R. E., et al., *Leukocyte activation induces surface redistribution of P-selectin glycoprotein ligand-1*. J Leukoc Biol, 1997. 61(4): p. 489-99.

49. Lorant, D. E., et al., *Activation of polymorphonuclear leukocytes reduces their adhesion to P-selectin and causes redistribution of ligands for P-selectin on their surfaces*. J Clin Invest, 1995. 96(1): p. 171-82.

50. Dore, M., et al., *Chemoattractant-induced changes in surface expression and redistribution of a functional ligand for P-selectin on neutrophils*. Blood, 1996. 87(5): p. 2029-37.

51. Picker, L. J., et al., *The neutrophil selectin LECAM-1 presents carbohydrate ligands to the vascular selectins ELAM-1 and GMP-140*. Cell, 1991. 66(5): p. 921-33.

52. Bargatze, R. F., et al., *Neutrophils roll on adherent neutrophils bound to cytokine-induced endothelial cells via L-selectin on the rolling cells*. J Exp Med, 1994. 180(5): p. 1785-92.

53. Simon, S. I., et al., *Beta 2-integrin and L-selectin are obligatory receptors in neutrophil aggregation*. Blood, 1993. 82(4): p. 1097-106.

54. Alon, R., et al., *Interactions through L-selectin between leukocytes and adherent leukocytes nucleate rolling adhesions on selectins and VCAM-1 in shear flow*. J Cell Biol, 1996. 135(3): p. 849-65.

55. Fuhlbrigge, R. C., et al., *Sialylated, fucosylated ligands for L-selectin expressed on leukocytes mediate tethering and rolling adhesions in physiologic flow conditions*. J Cell Biol, 1996. 135(3): p. 837-48.

56. Zollner, O., et al., *L-selectin from human, but not from mouse neutrophils binds directly to E-selectin*. J Cell Biol, 1997. 136(3): p. 707-16.

57. Snapp, K. R., et al., *P-selectin glycoprotein ligand-1 is essential for adhesion to P-selectin but not E-selectin in stably transfected hematopoietic cell lines*. Blood, 1997. 89(3): p. 896-901.

58. Sriramarao, P., et al., *E-selectin preferentially supports neutrophil but not eosinophil rolling under conditions of flow in vitro and in vivo*. J Immunol, 1996. 157(10): p. 4672-80.

59. Rainger, G. E., et al., *Cross-talk between cell adhesion molecules regulates the migration velocity of neutrophils*. Curr Biol, 1997. 7(5): p. 316-25.

60. Haller, H., et al., *T cell adhesion to P-selectin induces tyrosine phosphorylation of pp125 focal adhesion kinase and other substrates*. J Immunol, 1997. 158(3): p. 1061-7.

61. Lin, T. H., et al., *The role of protein tyrosine phosphorylation in integrin-mediated gene induction in monocytes*. J Cell Biol, 1994. 126(6): p. 1585-93.

62. Hidari, K. I., et al., *Engagement of P-selectin glycoprotein ligand-1 enhances tyrosine phosphorylation and activates mitogen-activated protein kinases in human neutrophils*. J Biol Chem, 1997. 272(45): p. 28750-6.

63. Laudanna, C., et al., *Sulfatides trigger increase of cytosolic free calcium and enhanced expression of tumor necrosis factor-alpha and interleukin-8 mRNA in human neutrophils. Evidence for a role of L-selectin as a signaling molecule*. J Biol Chem, 1994. 269(6): p. 4021-6.

64. Waddell, T. K., et al., *Potentiation of the oxidative burst of human neutrophils. A signaling role for L-selectin*. J Biol Chem, 1994. 269(28): p. 18485-91.

65. Hwang, S. T., et al., *GlyCAM-1, a physiologic ligand for L-selectin, activates beta 2 integrins on naive peripheral lymphocytes*. J Exp Med, 1996. 184(4): p. 1343-8.

66. Brenner, B., et al., *L-selectin activates the Ras pathway via the tyrosine kinase p56lck*. Proc Natl Acad Sci USA, 1996. 93(26): p. 15376-81.

67. Waddell, T. K., et al., *Signaling functions of L-selectin. Enhancement of tyrosine phosphorylation and activation of MAP kinase*. J Biol Chem, 1995. 270(25): p. 15403-11.

68. Simon, S. I., et al., *L-selectin (CD62L) cross-linking signals neutrophil adhesive functions via the Mac-1 (CD11b/CD18) beta 2-integrin*. J Immunol, 1995. 155(3): p. 1502-14.

69. Norman, K. E., et al., *Leukocyte rolling in vivo is mediated by P-selectin glycoprotein ligand-1*. Blood, 1995. 86(12): p. 4417-21.

70. Takada, M., et al., *The cytokine-adhesion molecule cascade in ischemia/reperfusion injury of the rat kidney. Inhibition by a soluble P-selectin ligand*. J Clin Invest, 1997. 99(11): p. 2682-90.

71. Frenette, P. S., et al., *Double knockout highlights value of endothelial selectins*. Immunol Today, 1996. 17(5): p. 205.

72. Snapp, K. R., et al., *A novel P-selectin glycoprotein ligand-1 monoclonal antibody recognizes an epitope within the tyrosine sulfate motif of human PSGL-1 and blocks recognition of both P- and L-selectin*. Blood, 1998. 91 (1): p. 154-64.

73. Thatte, A., et al., *Binding of function-blocking mAbs to mouse and human P-selectin glycoprotein ligand-1 peptides with and without tyrosine sulfation*. J Leukoc Biol, 2002. 72(3): p. 470-7.

74. Swers, J. S., et al., *A high affinity human antibody antagonist of P-selectin mediated rolling*. Biochem Biophys Res Commun, 2006. 350(3): p. 508-13.

75. Veerman, K. M., et al., *Interaction of the selectin ligand PSGL-1 with chemokines CCL21 and CCL19 facilitates efficient homing of T cells to secondary lymphoid organs*. Nat Immunol, 2007. 8(5): p. 532-9.

76. Hirata, T., et al., *Human P-selectin glycoprotein ligand-1 (PSGL-1) interacts with the skin-associated chemokine CCL27 via sulfated tyrosines at the PSGL-1 amino terminus*. J Biol Chem, 2004. 279(50): p. 51775-82.

77. Rollins, B. J., *Chemokines*. Blood, 1997. 90(3): p. 909-28.

78. Rossi, D. and A. Zlotnik, *The biology of chemokines and their receptors*. Annu Rev Immunol, 2000. 18: p. 217-42.

79. Zlotnik, A., J. Morales, and J. A. Hedrick, *Recent advances in chemokines and chemokine receptors*. Crit Rev Immunol, 1999. 19(1): p. 1-47.

80. Murphy, P. M., et al., *International union of pharmacology. XXII. Nomenclature for chemokine receptors*. Pharmacol Rev, 2000. 52(1): p. 145-76.

81. Moore, B. B., et al., *CXC chemokine modulation of angiogenesis: the importance of balance between angiogenic and angiostatic members of the family*. J Investig Med, 1998. 46(4): p. 113-20.

82. Salcedo, R., et al., *Vascular endothelial growth factor and basic fibroblast growth factor induce expression of*

83. Luster, A. D., *Chemokines—chemotactic cytokines that mediate inflammation.* N Engl J Med, 1998. 338(7): p. 436-45.

84. Bazan, J. F., et al., *A new class of membrane-bound chemokine with a CX3C motif* Nature, 1997. 385(6617): p. 640-4.

85. Matloubian, M., et al., *A transmembrane CXC chemokine is a ligand for HIV-coreceptor Bonzo.* Nat Immunol, 2000. 1(4): p. 298-304.

86. Horuk, R., *Chemokine receptors.* Cytokine Growth Factor Rev, 2001. 12(4): p. 313-35.

87. Horuk, R., et al., *The human erythrocyte inflammatory peptide (chemokine) receptor. Biochemical characterization, solubilization, and development of a binding assay for the soluble receptor.* Biochemistry, 1993. 32(22): p. 5733-8.

88. Neote, K., et al., *Identification of a promiscuous inflammatory peptide receptor on the surface of red blood cells.* J Biol Chem, 1993. 268(17): p. 12247-9.

89. Nibbs, R. J., et al., *Cloning and characterization of a novel promiscuous human beta-chemokine receptor D6.* J Biol Chem, 1997. 272(51): p. 32078-83.

90. Cyster, J. G., *Chemokines and cell migration in secondary lymphoid organs.* Science, 1999. 286(5447): p. 2098-102.

91. Baekkevold, E. S., et al., *The CCR7 ligand elc (CCL19) is transcytosed in high endothelial venules and mediates T cell recruitment.* J Exp Med, 2001. 193(9): p. 1105-12.

92. Reif, K., et al., *Balanced responsiveness to chemoattractants from adjacent zones determines B-cell position.* Nature, 2002. 416(6876): p. 94-9.

93. Muller, G., U. E. Hopken, and M. Lipp, *The impact of CCR7 and CXCR5 on lymphoid organ development and systemic immunity.* Immunol Rev, 2003. 195: p. 117-35.

94. Gerard, C. and B. J. Rollins, *Chemokines and disease.* Nat Immunol, 2001. 2(2): p. 108-15.

95. Standiford, T. J., et al., *Macrophage inflammatory protein-1 alpha mediates lung leukocyte recruitment, lung capillary leak, and early mortality in murine endotoxemia.* J Immunol, 1995. 155(3): p. 1515-24.

96. VanOtteren, G. M., et al., *Compartmentalized expression of RANTES in a murine model of endotoxemia.* J Immunol, 1995. 154(4): p. 1900-8.

97. Standiford, T. J., et al., *Neutralization of IL-10 increases lethality in endotoxemia. Cooperative effects of macrophage inflammatory protein-2 and tumor necrosis factor.* J Immunol, 1995. 155(4): p. 2222-9.

98. Greenberger, M. J., et al., *Neutralization of IL-10 increases survival in a murine model of Klebsiella pneumonia.* J Immunol, 1995. 155(2): p. 722-9.

99. Tsai, W. C., et al., *Lung-specific transgenic expression of KC enhances resistance to Klebsiella pneumoniae in mice.* J Immunol, 1998. 161(5): p. 2435-40.

100. Lukacs, N. W., *Role of chemokines in the pathogenesis of asthma.* Nat Rev Immunol, 2001. 1(2): p. 108-16.

101. D'Ambrosio, D., et al., *Chemokines and their receptors guiding T lymphocyte recruitment in lung inflammation.* Am J Respir Crit Care Med, 2001. 164(7): p. 1266-75.

102. Saetta, M., et al., *Increased expression of the chemokine receptor CXCR3 and its ligand CXCL10 in peripheral airways of smokers with chronic obstructive pulmonary disease.* Am J Respir Crit Care Med, 2002. 165(10): p. 1404-9.

103. Medoff, B. D., et al., *IFN-gamma-inducible protein 10 (CXCL10) contributes to airway hyperreactivity and airway inflammation in a mouse model of asthma.* J Immunol, 2002. 168(10): p. 5278-86.

104. Ross, R., *Atherosclerosis—an inflammatory disease.* N Engl J Med, 1999. 340(2): p. 115-26.

105. Burke-Gaffney, A., A. V. Brooks, and R. G. Bogle, *Regulation of chemokine expression in atherosclerosis.* Vascul Pharmacol, 2002. 38(5): p. 283-92.

106. McDermoft, D. H., et al., *Association between polymorphism in the chemokine receptor CX3CR1 and coronary vascular endothelial dysfunction and atherosclerosis.* Circ Res, 2001. 89(5): p. 401-7.

107. Moatti, D., et al., *Polymorphism in the fractalkine receptor CX3CR1 as a genetic risk factor for coronary artery disease.* Blood, 2001. 97(7): p. 1925-8.

108. McDermott, D. H., et al., *Chemokine receptor mutant CX3CR1-M280 has impaired adhesive function and correlates with protection from cardiovascular disease in humans.* J Clin Invest, 2003. 111(8): p. 1241-50.

109. Szekanecz, Z., et al., *Chemokines in rheumatoid arthritis.* Springer Semin Immunopathol, 1998. 20(1-2): p. 115-32.

110. Szekanecz, Z. and A. E. Koch, *Chemokines and angiogenesis.* Curr Opin Rheumatol, 2001. 13(3): p. 202-8.

111. Nanki, T., et al., *Stromal cell-derived factor-1-CXC chemokine receptor 4 interactions play a central role in CD4+T cell accumulation in rheumatoid arthritis synovium.* J Immunol, 2000. 165(11): p. 6590-8.

112. Traugoft, U., E. L. Reinherz, and C. S. Raine, *Multiple sclerosis: distribution of T cell subsets within active chronic lesions.* Science, 1983. 219(4582): p. 308-10.

113. McManus, C., et al., *MCP-1, MCP-2 and MCP-3 expression in multiple sclerosis lesions: an immunohistochemical and in situ hybridization study.* J Neuroimmunol, 1998. 86(1): p. 20-9.

114. Sorensen, T. L. and F. Sellebjerg, *Distinct chemokine receptor and cytokine expression profile in secondary progressive MS.* Neurology, 2001. 57(8): p. 1371-6.

115. Balashov, K. E., et al., *CCR5(+) and CXCR3(+) T cells are increased in multiple sclerosis and their ligands MIP-1 alpha and IP-10 are expressed in demyelinating brain lesions.* Proc Natl Acad Sci USA, 1999. 96(12): p. 6873-8.

116. Simpson, J., et al., *Expression of the beta-chemokine receptors CCR2, CCR3 and CCR5 in multiple sclerosis central nervous system tissue.* J Neuroimmunol, 2000. 108(1-2): p. 192-200.

117. Godiska, R., et al., *Chemokine expression in murine experimental allergic encephalomyelitis.* J Neuroimmunol, 1995. 58(2): p. 167-76.

118. Karpus, W. J. and K. J. Kennedy, *MIP-1 alpha and MCP-1 differentially regulate acute and relapsing autoimmune encephalomyelitis as well as Th1/Th2 lymphocyte differentiation.* J Leukoc Biol, 1997. 62(5): p. 681-7.

119. Liu, M. T., H. S. Keirstead, and T. E. Lane, *Neutralization of the chemokine CXCL10 reduces inflammatory cell invasion and demyelination and improves neurological function in a viral model of multiple sclerosis.* J Immunol, 2001. 167(7): p. 4091-7.

120. Izikson, L., et al., *Resistance to experimental autoimmune encephalomyelitis in mice lacking the CC chemokine receptor (CCR)2.* J Exp Med, 2000. 192(7): p. 1075-80.

121. Rottman, J. B., et al., *Leukocyte recruitment during onset of experimental allergic encephalomyelitis is CCR1 dependent*. Eur J Immunol, 2000. 30(8): p. 2372-7.

122. Middel, P., et al., *Increased number of mature dendritic cells in Crohn's disease: evidence for a chemokine mediated retention mechanism*. Gut, 2006. 55(2): p. 220-7.

123. Kawashima, D., et al., *Augmented expression of secondary lymphoid tissue chemokine and EBI1 ligand chemokine in Crohn's disease*. J Clin Pathol, 2005. 58(10): p. 1057-63.

124. Feldhaus M J, Siegel R W, Opresko L K, Coleman J R, Feldhaus J M, Yeung Y A, Cochran J R, Heinzelman P, Colby D, Swers J, Graff C, Wiley H S, Wittrup K D. Flow-cytometric isolation of human antibodies from a nonimmune *Saccharomyces cerevisiae* surface display library. Nat Biotechnol., 2003. 21 (2):163-70. PMID: 12536217.

125. Swers, J. S., Isolation and Engineering of a High Affinity Antibody Against P-selectin Glycoprotein Ligand-1 (PSGL-1). 2005. Ph.D. Thesis, MIT.

126. Inoue, et al., "Blockade of PSGL-1 attenuates DC14+ monocytic cell recruitment in intestinal mucosa and ameliorates ileitis in SAMP1/Yit mice," *Journal of Leukocyte Biology*, (March 2005) Vol. 77, pp. 287-295.

127. Marini, M., et al., TNFα neutralization ameliorates the severity of murine Crohn's-like ileitis by abrogation of intestinal epithelial cell apoptosis. 2003, PNAS Vol. 100 (14): 83366-8371.

What is claimed is:

1. A method of inhibiting PSGL-1-mediated adhesion and chemokine-mediated migration of human leukocytes, lymphocytes or endothelial cells, comprising:
providing a PSGL-1-specific monoclonal antibody or a binding fragment thereof which binds with high affinity to a sulfated N-terminal portion of human PSGL-1 comprising at least a portion of amino acids 42-62 of SEQ ID NO:1; and
exposing the antibody or binding fragment thereof to PSGL-1-bearing human leukocytes, lymphocytes or endothelial cells wherein the antibody or binding fragment thereof binds to the sulfated N-terminal portion of the human PSGL-1 on the human leukocytes, lymphocytes or endothelial cells and blocks the binding of P-selectin and/or L-selectin to the human PSGL-1 on the human leukocytes, lymphocytes, or endothelial cells and blocks the binding of at least one of chemokines CCL19, CCL21, CCL27 and CCL28 to the human PSGL-1 on the human leukocytes, lymphocytes or endothelial cells, thereby inhibiting both adhesion and chemotactic migration of the human leukocytes, lymphocytes or endothelial cells.

2. The method of claim 1 wherein the antibody or binding fragment thereof comprises variable heavy chain CDRs having amino acid sequences SEQ ID NO:6, SEQ ID NO:7, and SEQ ID NO:8, and variable light chain CDRs having amino acid sequences SEQ ID NO:9, SEQ ID NO:10, and SEQ ID NO:11 and comprises a constant chain comprising a $IgG_2$ constant chain, and which does not activate complement via the classical pathway by interacting with C1Q.

3. The method of claim 1 wherein the dual function anti-PSGL-1 antibody or binding fragment thereof binds to PSGL-1 with a $K_d$ of $\leq 100$ nM.

4. A method of treating a subject in need of treatment for an inflammatory condition arising from an inflammatory process involving PSGL-1-mediated adhesion, comprising:
administering to the subject an amount of a dual function anti-PSGL-1 antibody or binding fragment thereof that binds with high affinity to a sulfated N-terminal portion of human PSGL-1 comprising at least a portion of amino acids 42-62 of SEQ ID NO:1 and competitively blocks P-selectin and/or L-selectin binding to human PSGL-1 and competitively blocks the binding of at least one of chemokines CCL19, CCL21, CCL27 and CCL28 to human PSGL-1, and is effective in mitigating the inflammatory condition in the subject wherein the inflammatory condition is at least one of an inflammatory bowel disease, graft rejection, asthma, a chronic obstructive pulmonary disease, psoriasis, a thrombosis, a dermatitis, nephritis, lupus erythematosis, scleroderma, rhinitis, anaphylaxis, atherosclerosis, an allergic reaction, thyroiditis, and arthritis.

5. The method of claim 4 wherein the dual function anti-PSGL-1 antibody or binding fragment thereof is a human monoclonal antibody or fragment thereof, or a humanized monoclonal antibody or a fragment thereof.

6. The method of claim 4 wherein the dual function anti-PSGL-1 antibody or binding fragment thereof is administered to the subject parenterally, intravenously, subcutaneously or in a nebulized form.

7. The method of claim 4 wherein the dual function anti-PSGL-1 antibody or binding fragment thereof is administered in the amount of about 0.1-100 mg/kg.

8. The method of claim 1 wherein the dual function anti-PSGL-1 antibody or binding fragment thereof binds to PSGL-1 with a $K_d$ of $\leq 100$ nM.

9. The method of claim 4 wherein the dual function anti-PSGL-1 antibody or antigen-binding fragment thereof does not activate complement via the classical pathway by interacting with C1Q.

10. The method of claim 4 wherein the dual function anti-PSGL-1 antibody or antigen-binding fragment thereof does not bind to Fc receptors.

11. The method of claim 4 wherein the dual function anti-PSGL-1 antibody or antigen-binding fragment does not express effector function as defined by activation of complement or binding of Fc receptors.

12. The method of claim 1 wherein the PSGL-1-specific monoclonal antibody or binding fragment thereof is a humanized monoclonal antibody or a fragment thereof.

13. The method of claim 1 wherein the PSGL-1-specific monoclonal antibody or binding fragment thereof does not bind to FC receptors.

14. The method of claim 1 wherein the PSGL-1-specific monoclonal antibody or binding fragment thereof does not express effector function as defined by activation of complement or binding of FC receptors.

15. The method of claim 1 wherein the PSGL-1-mediated adhesion and chemokine-mediated migration of the human leukocytes, lymphocytes or endothelial cells involves a condition involving at least one of an inflammatory bowel disease, graft rejection, asthma, a chronic obstructive pulmonary disease, psoriasis, a thrombosis, arthritis, a dermatitis, nephritis, lupus erythematosis, scleroderma, rhinitis, anaphylaxis, atherosclerosis, an allergic reaction, and thyroiditis.

16. A method of inhibiting PSGL-1-mediated adhesion and chemokine-mediated migration of human leukocytes, lymphocytes or endothelial cells, comprising:
providing a PSGL-1-specific monoclonal antibody or a binding fragment thereof which binds with high affinity to a sulfated N-terminal portion of human PSGL-1 comprising at least a portion of amino acids 42-62 of SEQ ID NO:1, and which does not express effector function as defined by activation of complement or binding of FC receptors; and
exposing the antibody or binding fragment thereof to PSGL-1-bearing human leukocytes, lymphocytes or endothelial cells wherein the antibody or binding fragment thereof binds to the sulfated N-terminal portion of the human PSGL-1 on the human leukocytes, lymphocytes or endothelial cells and blocks the binding of P-selectin and/or L-selectin to the human PSGL-1 on the human leukocytes, lymphocytes, or endothelial cells and blocks the binding of at least one of chemokines CCL19, CCL21, CCL27 and CCL28 to the human PSGL-1 on the human leukocytes, lymphocytes or endothelial cells, thereby inhibiting both adhesion and chemotactic migration of the human leukocytes, lymphocytes or endothelial cells.

17. The method of claim 16 wherein the antibody or binding fragment thereof comprises variable heavy chain CDRs having amino acid sequences SEQ ID NO:6, SEQ ID NO:7, and SEQ ID NO:8, and variable light chain CDRs having amino acid sequences SEQ ID NO:9, SEQ ID NO:10, and SEQ ID NO:11 and comprises a constant chain comprising a IgG$_2$ constant chain, and which does not activate complement via the classical pathway by chemonkines CCL19, CCL27, and CCL28 to the human PSGL-1 on the human leukocytes, lymphocytes or endothelial cells, and is the therby able to inhibit both adhesion and cheotactic migration of the human leukocytes, lymphocytes or endothelial cells.

18. The method of claim 16 wherein the dual function anti-PSGL-1 antibody or binding fragment thereof binds to PSGL-1 with a K$_d$ of ≦100 nM.

19. The method of claim 16 wherein the dual function anti-PSGL-1 antibody or binding fragment thereof is a human monoclonal antibody or fragment thereof, or a humanized monoclonal antibody or a fragment thereof.

20. The method of claim 16 wherein the PSGL-1-mediated adhesion and chemokine-mediated migration of the human leukocytes, lymphocytes or endothelial cells involves a condition involving at least one of an inflammatory bowel disease, graft rejection, asthma, a chronic obstructive pulmonary disease, psoriasis, a thrombosis, arthritis, a dermatitis, nephritis, lupus erythematosis, scleroderma, rhinitis, anaphylaxis, atherosclerosis, an allergic reaction, and thyroiditis.

21. A PSGL-1-specific monoclonal antibody or binding fragment thereof which binds with high affinity to a sulfated N-terminal portion of human PSGL-1 which comprises at least a portion of amino acids 42-62 of SEQ ID NO:1, and which does not express effector function as defined by activation of complement or binding of FC receptors, and which, when exposed to PSGL-1-bearing human leukocytes, lymphocytes or endothelial cells, binds to the sulfated N-terminal portion of the human PSGL-1 on the human leukocytes, lymphocytes or endothelial cells and blocks the binding of P-selectin and/or L-selectin to the human PSGL-1 on the human leukocytes, lymphocytes, or endothelial cells and blocks the binding of at least one of chemokines CCL19, CCL21, CCL27 and CCL28 to the human PSGL-1 on the human leukocytes, lymphocytes or endothelial cells, and is thereby able to inhibit both adhesion and chemotactic migration of the human leukocytes, lymphocytes or endothelial cells.

22. The PSGL-1-specific monoclonal antibody or binding fragment thereof of claim 21 comprising variable heavy chain CDRs having amino acid sequences SEQ ID NO:6, SEQ ID NO:7, and SEQ ID NO:8, and variable light chain CDRs having amino acid sequences SEQ ID NO:9, SEQ ID NO:10, and SEQ ID NO:11 and comprising a constant chain comprising an IgG$_2$ constant chain.

23. The PSGL-1-specific monoclonal antibody or binding fragment thereof of claim 21 which is able to bind to PSGL-1 with a K$_d$ of ≦100 nM.

24. The PSGL-1-specific monoclonal antibody or binding fragment thereof of claim 21 which is able to bind to PSGL-1 with a K$_d$ of ≦50 nM.

25. The PSGL-1-specific monoclonal antibody or binding fragment thereof of claim 21 which is able to bind to PSGL-1 with a K$_d$ of ≦25 nM.

26. The PSGL-1-specific monoclonal antibody or binding fragment thereof of claim 21 which is able to bind to PSGL-1 with a K$_d$ of ≦10 nM.

27. The PSGL-1-specific monoclonal antibody or binding fragment thereof of claim 21 which is able to bind to PSGL-1 with a K$_d$ of ≦5 nM.

28. The PSGL-1-specific monoclonal antibody or binding fragment thereof of claim 21 comprising a human monoclonal antibody or fragment thereof, or a humanized monoclonal antibody or a fragment thereof.

29. A composition comprising the PSGL-1-specific monoclonal antibody or binding fragment thereof of claim 21 disposed within a pharmaceutically-acceptable carrier or vehicle.

* * * * *

UNITED STATES PATENT AND TRADEMARK OFFICE
CERTIFICATE OF CORRECTION

PATENT NO. : 7,833,530 B2
APPLICATION NO. : 12/467060
DATED : November 16, 2010
INVENTOR(S) : Richard Alvarez and Scott Rollins Page 1 of 1

It is certified that error appears in the above-identified patent and that said Letters Patent is hereby corrected as shown below:

Column 19, line 35: Delete "Left." and replace with -- Lett. --
Column 34, line 63: Delete "Zanneftino," and replace with -- Zannettino, --
Column 38, line 11: Delete "McDermoft," and replace with -- McDermott, --
Column 38, line 33: Delete "Traugoft," and replace with -- Traugott, --

In the Claims:
Column 59, line 38 through 42: Delete "chemonkines CCL19, CCL27, and CCL28 to the human PSGL-1 on the human leukocytes, lymphocytes or endothelial cells, and is the therby able to inhibit both adhesion and cheotactic migration of the human leukocytes, lymphocytes or endothelial cells." and insert -- interacting with CIQ. --

Signed and Sealed this
Twenty-second Day of March, 2011

David J. Kappos
*Director of the United States Patent and Trademark Office*